United States Patent [19]

Slusher et al.

[11] Patent Number: 5,824,662
[45] Date of Patent: *Oct. 20, 1998

[54] TREATMENT OF GLOBAL AND FOCAL ISCHEMIA USING NAALADASE INHIBITORS

[75] Inventors: Barbara S. Slusher, Kingsville; Paul F. Jackson, Bel Air, both of Md.

[73] Assignee: Guilford Pharmaceuticals Inc., Baltimore, Md.

[*] Notice: The term of this patent shall not extend beyond the expiration date of Pat. No. 5,672,592.

[21] Appl. No.: 718,703

[22] Filed: Sep. 27, 1996

[51] Int. Cl.$^6$ .............................. C07F 9/38; C07F 9/58; A61K 31/65

[52] U.S. Cl. .................................. 514/75; 562/8; 562/12; 546/21; 546/22; 548/413; 549/5; 549/6; 549/216; 549/218

[58] Field of Search ..................................... 514/574, 921, 514/75

[56] References Cited

U.S. PATENT DOCUMENTS

| | | |
|---|---|---|
| H1312 | 5/1994 | Coughlin et al. . |
| 4,671,958 | 6/1987 | Rodwell et al. . |
| 4,741,900 | 5/1988 | Alvarez et al. . |
| 4,853,326 | 8/1989 | Quash et al. . |
| 4,867,973 | 9/1989 | Goers . |
| 4,906,779 | 3/1990 | Weber et al. . |
| 4,918,064 | 4/1990 | Cordi et al. . |
| 4,937,183 | 6/1990 | Ultee et al. . |
| 4,950,738 | 8/1990 | King et al. . |
| 4,959,493 | 9/1990 | Ohfume et al. . |
| 4,966,999 | 10/1990 | Coughlin et al. . |
| 4,977,155 | 12/1990 | Jacobsen et al. . |
| 4,980,356 | 12/1990 | Audiau et al. . |
| 4,994,446 | 2/1991 | Sokolovsky et al. . |
| 5,011,834 | 4/1991 | Weber et al. . |
| 5,026,717 | 6/1991 | Audiau et al. . |
| 5,047,227 | 9/1991 | Rodwell et al. . |
| 5,057,516 | 10/1991 | Jacobsen et al. . |
| 5,068,238 | 11/1991 | Jimonet . |
| 5,075,306 | 12/1991 | Jacobsen et al. . |
| 5,079,250 | 1/1992 | Jacobsen et al. . |
| 5,093,525 | 3/1992 | Weber et al. . |
| 5,109,001 | 4/1992 | Jacobsen et al. . |
| 5,130,330 | 7/1992 | Bowen et al. . |
| 5,135,080 | 8/1992 | Miller et al. . |

(List continued on next page.)

FOREIGN PATENT DOCUMENTS

| | | |
|---|---|---|
| 8937077 | 1/1990 | Australia . |
| 8946189 | 6/1990 | Australia . |
| 9054488 | 11/1990 | Australia . |
| 9066624 | 5/1991 | Australia . |
| 90673393 | 5/1991 | Australia . |
| 9175796 | 9/1991 | Australia . |
| 9185131 | 3/1992 | Australia . |
| 9187666 | 5/1992 | Australia . |
| 9189297 | 5/1992 | Australia . |
| 645766 | 1/1994 | Australia . |
| 9345401 | 1/1994 | Australia . |
| 9464063 | 2/1994 | Australia . |
| 9348014 | 3/1994 | Australia . |
| 9461310 | 8/1994 | Australia . |
| 652555 | 9/1994 | Australia . |
| 947047 | 12/1994 | Australia . |
| 656154 | 1/1995 | Australia . |
| 9471882 | 1/1995 | Australia . |
| 9510551 | 5/1995 | Australia . |
| 9479151 | 6/1995 | Australia . |
| 9514474 | 7/1995 | Australia . |
| 9519457 | 10/1995 | Australia . |
| 9522125 | 10/1995 | Australia . |
| 9528530 | 2/1996 | Australia . |
| 9530357 | 3/1996 | Australia . |
| 9532781 | 3/1996 | Australia . |

(List continued on next page.)

OTHER PUBLICATIONS

Slusher et al., "Rat Brain N–Acetylated α–Linked Acidic Dipeptidase Activity," J. Bio. Chem., 1990, 265 (34), 21297–21301.

Tsai et al., 61st Salmon Lecturer of the New York Academy of Medicine, Dec. 2–3, 1993, "Changes of Excitatory Neurotransmitter Metabolism in Schizophrenic Brains."

Tsai et al., "Reductions in acidic amino acids and N–acetylaspartylglutamate in amyotrophic lateral sclerosis CNS," Brain Research, 556, 1991, 151–156.

Rothstein et al., "Abnormal Excitatory Amino Acid Metabolism in Amyotrophic Lateral Sclerosis," Ann Neurol, 1990, 28, 18–25.

Tsai et al., "Immunocytochemical Distribution of N–acetylaspartylglutamate in the Rat Forbrain and Glutamatergic Pathways," J. Chem. Neuroanatomy, 1993, vol. 6, 277–292.

Subasinghe et al., Synthesis of Acyclic and Dehydroaspartic Acid Analogues of Ac–Asp–Glu–OH and Their Inhibition of Rat Brain N–Acetylated α–Linked Acidic Dipeptidase (NAALA Dipeptidase), J. Med. Chem 1990, 33, 2734–2744.

Slusher et al., Immunocytochemical Localization of the N–Acetyl–Aspartyl–Glutamate (NAAG) Hydrolyzing Enzyme N–Acetylated α–Linked Acidic Dipeptidase (NAALADase), J. Comparative Neurology, 1992, 315:217–229.

Stauch et al., "The effects of N–acetylated alpha–linked acidic dipeptidase (NAALADase) inhibitors on [$^3$H] NAAG catabolism in vivo," Neuroscience Letters, 1989, 100, 295–300.

(List continued on next page.)

Primary Examiner—Keith D. MacMillian
Attorney, Agent, or Firm—Gary M. Nath; Todd L. Juneau; Nath & Associates

[57] ABSTRACT

The present invention includes compositions and methods of treatment for glutamate abnormalities and associated nervous tissue insult in a animal by inhibition of NAALADase enzyme. Compositions include glutamate-derived hydroxyphosphinyl derivative compounds, acidic peptide analogs, phosphinic acid derivatives and mixtures thereof that inhibit NAALADase enzyme activity and their use for treating glutamate abnormalities such as created by global and focal ischemia.

12 Claims, 5 Drawing Sheets

U.S. PATENT DOCUMENTS

| | | |
|---|---|---|
| 5,140,104 | 8/1992 | Coughlin et al. . |
| 5,145,862 | 9/1992 | Aizenman et al. . |
| 5,156,840 | 10/1992 | Goers et al. . |
| 5,158,976 | 10/1992 | Rosenberg . |
| 5,162,504 | 11/1992 | Horoszewicz . |
| 5,162,512 | 11/1992 | King et al. . |
| 5,177,109 | 1/1993 | Cordi et al. . |
| 5,190,976 | 3/1993 | Weber et al. . |
| 5,196,439 | 3/1993 | Higurashi et al. . |
| 5,196,510 | 3/1993 | Rodwell et al. . |
| 5,236,940 | 8/1993 | Phone-Poulenc Sante . |
| 5,242,915 | 9/1993 | Ueda et al. . |
| 5,262,568 | 11/1993 | Weber et al. . |
| 5,283,244 | 2/1994 | Yamnouchi . |
| 5,284,867 | 2/1994 | Benita et al. . |
| 5,292,765 | 3/1994 | Choi et al. . |
| 5,326,856 | 7/1994 | Coughlin et al. . |
| 5,336,689 | 8/1994 | Weber et al. . |
| 5,340,824 | 8/1994 | Gueremy et al. . |
| 5,356,902 | 10/1994 | Orstein . |
| 5,403,837 | 4/1995 | Audiau et al. . |
| 5,403,861 | 4/1995 | Fischer . |
| 5,434,159 | 7/1995 | De-Haven-Hudkins et al. . |
| 5,438,130 | 8/1995 | McCormick et al. . |
| 5,449,761 | 9/1995 | Belinka, Jr. et al. . |
| 5,459,037 | 10/1995 | Erlander et al. . |
| 5,473,077 | 12/1995 | Monn et al. . |
| 5,474,547 | 12/1995 | Aebischer et al. . |
| 5,478,859 | 12/1995 | Drejer et al. . |
| 5,486,620 | 1/1996 | Monn . |
| 5,489,525 | 2/1996 | Pastan . |
| 5,489,717 | 2/1996 | Bigge et al. . |
| 5,491,241 | 2/1996 | Monn . |
| 5,495,042 | 2/1996 | Belinka, Jr. et al. . |
| 5,500,420 | 3/1996 | Maiese . |
| 5,502,166 | 3/1996 | Mishina . |
| 5,521,215 | 5/1996 | Benita et al. . |
| 5,523,307 | 6/1996 | Higurashi et al. . |
| 5,527,885 | 6/1996 | Cooughlin et al. . |
| 5,536,721 | 7/1996 | Faarup et al. . |
| 5,594,007 | 1/1997 | Chenard . |
| 5,672,592 | 9/1997 | Jackson et al. ............ 514/75 |

FOREIGN PATENT DOCUMENTS

| | | |
|---|---|---|
| 9533251 | 3/1996 | Australia . |
| 9533252 | 3/1996 | Australia . |
| 9534142 | 3/1996 | Australia . |
| 9534186 | 3/1996 | Australia . |
| 9005758 | 9/1991 | Brazil . |
| 94048098 | 8/1995 | Brazil . |
| 9503638 | 5/1996 | Brazil . |
| 2005590 | 6/1990 | Canada . |
| 2005592 | 6/1990 | Canada . |
| 2029419 | 5/1991 | Canada . |
| 2029974 | 5/1991 | Canada . |
| 13045056 | 7/1992 | Canada . |
| 1306995 | 9/1992 | Canada . |
| 2068918 | 11/1992 | Canada . |
| 1326670 | 2/1994 | Canada . |
| 2117852 | 4/1995 | Canada . |
| 1369074 | 6/1995 | Canada . |
| 2156024 | 2/1996 | Canada . |
| 2157248 | 3/1996 | Canada . |
| 9605828 | 2/1996 | Cocos (Keeling) Islands . |
| 9402947 | 12/1995 | Czech Rep. . |
| 9502221 | 3/1996 | Czech Rep. . |
| 9502074 | 5/1996 | Czech Rep. . |
| 8806621 | 5/1989 | Denmark . |
| 8906334 | 6/1990 | Denmark . |
| 169383 | 10/1994 | Denmark . |
| 4084316 | of 0000 | European Pat. Off. . |
| 633779 | of 0000 | European Pat. Off. . |
| 652887 | of 0000 | European Pat. Off. . |
| 270290 | 6/1988 | European Pat. Off. . |
| 3130012 | 4/1989 | European Pat. Off. . |
| 31809 | 5/1989 | European Pat. Off. . |
| 342558 | 11/1989 | European Pat. Off. . |
| 348872 | 1/1990 | European Pat. Off. . |
| 370499 | 5/1990 | European Pat. Off. . |
| 374040 | 6/1990 | European Pat. Off. . |
| 374041 | 6/1990 | European Pat. Off. . |
| 2223569 | 9/1990 | European Pat. Off. . |
| 433112 | 6/1991 | European Pat. Off. . |
| 470127 | 2/1992 | European Pat. Off. . |
| 4084316 | 5/1992 | European Pat. Off. . |
| 486621 | 5/1992 | European Pat. Off. . |
| 497895 | 8/1992 | European Pat. Off. . |
| 509066 | 10/1992 | European Pat. Off. . |
| 375510 | 11/1992 | European Pat. Off. . |
| 517852 | 12/1992 | European Pat. Off. . |
| 519602 | 12/1992 | European Pat. Off. . |
| 528968 | 3/1993 | European Pat. Off. . |
| 530058 | 3/1993 | European Pat. Off. . |
| 556393 | 8/1993 | European Pat. Off. . |
| 516748 | 4/1994 | European Pat. Off. . |
| 592571 | 4/1994 | European Pat. Off. . |
| 594597 | 5/1994 | European Pat. Off. . |
| 4084347 | 6/1994 | European Pat. Off. . |
| 532602 | 8/1994 | European Pat. Off. . |
| 629615 | 12/1994 | European Pat. Off. . |
| 600278 | 1/1995 | European Pat. Off. . |
| 4275189 | 3/1995 | European Pat. Off. . |
| 648762 | 4/1995 | European Pat. Off. . |
| 667340 | 8/1995 | European Pat. Off. . |
| 669397 | 8/1995 | European Pat. Off. . |
| 688319 | 12/1995 | European Pat. Off. . |
| 318029 | 2/1996 | European Pat. Off. . |
| 696577 | 2/1996 | European Pat. Off. . |
| 699678 | 3/1996 | European Pat. Off. . |
| 703218 | 3/1996 | European Pat. Off. . |
| 705100 | 4/1996 | European Pat. Off. . |
| 707644 | 4/1996 | European Pat. Off. . |
| 711755 | 5/1996 | European Pat. Off. . |
| 713703 | 5/1996 | European Pat. Off. . |
| 715851 | 6/1996 | European Pat. Off. . |
| 8903170 | of 0000 | Finland . |
| 8905982 | 6/1990 | Finland . |
| 8905983 | 6/1990 | Finland . |
| 9005628 | 5/1991 | Finland . |
| 9301394 | 4/1993 | Finland . |
| 9301891 | 4/1993 | Finland . |
| 9301892 | 4/1993 | Finland . |
| 9301893 | 4/1993 | Finland . |
| 9404714 | 10/1994 | Finland . |
| 93106 | 11/1994 | Finland . |
| 93107 | 11/1994 | Finland . |
| 93108 | 11/1994 | Finland . |
| 93838 | 2/1995 | Finland . |
| 93839 | 2/1995 | Finland . |
| 93840 | 2/1995 | Finland . |
| 93841 | 2/1995 | Finland . |
| 9405704 | 6/1995 | Finland . |
| 9506353 | 12/1995 | Finland . |
| 9503837 | 2/1996 | Finland . |
| 9504066 | 3/1996 | Finland . |
| 9602000 | 5/1996 | Finland . |
| 2640622 | 6/1990 | France . |
| 2640624 | 6/1990 | France . |
| 2649701 | 1/1991 | France . |
| 2649703 | 1/1991 | France . |
| 2649705 | 1/1991 | France . |
| 2662160 | 11/1991 | France . |

| Number | Date | Country |
|---|---|---|
| 2662694 | 12/1991 | France . |
| 2662695 | 12/1991 | France . |
| 2678619 | 1/1993 | France . |
| 2707880 | 1/1995 | France . |
| 2726271 | 5/1996 | France . |
| 290883 | 6/1991 | German Dem. Rep. . |
| 68903484 | 12/1992 | Germany . |
| 68905585 | 4/1993 | Germany . |
| 4212529 | 10/1993 | Germany . |
| 68909513 | 11/1993 | Germany . |
| 3886003 | 1/1994 | Germany . |
| 68912822 | 3/1994 | Germany . |
| 69009604 | 7/1994 | Germany . |
| 69103271 | 9/1994 | Germany . |
| 69017839 | 4/1995 | Germany . |
| 4410822 | 9/1995 | Germany . |
| 3854991 | 3/1996 | Germany . |
| 69210106 | 5/1996 | Germany . |
| T53625 | 11/1990 | Hungary . |
| t54891 | 4/1991 | Hungary . |
| T55231 | 5/1991 | Hungary . |
| T55403 | 5/1991 | Hungary . |
| 208079 | 8/1993 | Hungary . |
| 208709 | 8/1993 | Hungary . |
| T64324 | 12/1993 | Hungary . |
| 210744 | 7/1995 | Hungary . |
| T69181 | 8/1995 | Hungary . |
| 62406 | 1/1995 | Ireland . |
| 62688 | 2/1995 | Ireland . |
| 64289 | 7/1995 | Ireland . |
| 64657 | 8/1995 | Ireland . |
| 84535 | 9/1992 | Israel . |
| 92710 | 6/1993 | Israel . |
| 92238 | 7/1995 | Israel . |
| 1217603 | 3/1990 | Italy . |
| 1238346 | 7/1993 | Italy . |
| 04178385 | of 0000 | Japan . |
| 1135790 | 5/1989 | Japan . |
| 1316356 | 12/1989 | Japan . |
| 2017157 | 1/1990 | Japan . |
| 2193922 | 7/1990 | Japan . |
| 2223570 | 9/1990 | Japan . |
| 2223571 | 9/1990 | Japan . |
| 3170491 | 7/1991 | Japan . |
| 3209377 | 9/1991 | Japan . |
| 3517229 | 11/1992 | Japan . |
| 4346927 | 12/1992 | Japan . |
| 5501540 | 3/1993 | Japan . |
| 5239098 | 9/1993 | Japan . |
| 5506012 | 9/1993 | Japan . |
| 5507062 | 10/1993 | Japan . |
| 5507918 | 11/1993 | Japan . |
| 5508147 | 11/1993 | Japan . |
| 5509077 | 12/1993 | Japan . |
| 94517862 | 1/1994 | Japan . |
| 6062861 | 3/1994 | Japan . |
| 6157597 | 6/1994 | Japan . |
| 6228112 | 8/1994 | Japan . |
| 6508843 | 10/1994 | Japan . |
| 6321805 | 11/1994 | Japan . |
| 95049425 | 5/1995 | Japan . |
| 7149724 | 6/1995 | Japan . |
| 95068235 | 7/1995 | Japan . |
| 71964533 | 8/1995 | Japan . |
| 7267908 | 10/1995 | Japan . |
| 8034771 | 2/1996 | Japan . |
| 8081469 | 3/1996 | Japan . |
| 236057 | 9/1994 | New Zealand . |
| 8902680 | 1/1990 | Norway . |
| 8905030 | 7/1990 | Norway . |
| 8905032 | 7/1990 | Norway . |
| 9004921 | 5/1991 | Norway . |
| 173060 | 7/1993 | Norway . |
| 174200 | 12/1993 | Norway . |
| 174775 | 3/1994 | Norway . |
| 9404578 | 6/1995 | Norway . |
| 9504888 | 12/1995 | Norway . |
| 9503191 | 2/1996 | Norway . |
| 9503394 | 3/1996 | Norway . |
| 92605 | of 0000 | Portugal . |
| 91010 | 12/1989 | Portugal . |
| 92604 | 6/1990 | Portugal . |
| 92606 | 6/1990 | Portugal . |
| 96930 | 11/1991 | Portugal . |
| 8909551 | 9/1990 | South Africa . |
| 8908936 | 7/1991 | South Africa . |
| 9008914 | 9/1991 | South Africa . |
| 9101553 | 12/1991 | South Africa . |
| 9302553 | of 1993 | South Africa . |
| 9403744 | 6/1995 | South Africa . |
| 9502431 | 2/1996 | South Africa . |
| 2043070 | 12/1993 | Spain . |
| 2052954 | 7/1994 | Spain . |
| 2054068 | 8/1994 | Spain . |
| 2055365 | 8/1994 | Spain . |
| 2057901 | 10/1994 | Spain . |
| 2059636 | 11/1994 | Spain . |
| 2060635 | 12/1994 | Spain . |
| 2061782 | 12/1994 | Spain . |
| 2062794 | 12/1994 | Spain . |
| 2071786 | 7/1995 | Spain . |
| 9012575 | 11/1990 | WIPO . |
| 9102810 | 3/1991 | WIPO . |
| 9106536 | 5/1991 | WIPO . |
| 9112797 | 9/1991 | WIPO . |
| 9117984 | 11/1991 | WIPO . |
| 9118892 | 12/1991 | WIPO . |
| 9204023 | 3/1992 | WIPO . |
| 9217168 | 4/1992 | WIPO . |
| 9207562 | 5/1992 | WIPO . |
| 9207847 | 5/1992 | WIPO . |
| 9301194 | 1/1993 | WIPO . |
| 9320820 | 10/1993 | WIPO . |
| 9325203 | 12/1993 | WIPO . |
| 9401142 | 1/1994 | WIPO . |
| 9418172 | 1/1994 | WIPO . |
| 9403469 | 2/1994 | WIPO . |
| 9404698 | 3/1994 | WIPO . |
| 9415622 | 7/1994 | WIPO . |
| 9420470 | 9/1994 | WIPO . |
| 9427591 | 12/1994 | WIPO . |
| 9501429 | 1/1995 | WIPO . |
| 9513369 | 5/1995 | WIPO . |
| 95076 | 7/1995 | WIPO . |
| 9518154 | 7/1995 | WIPO . |
| 9525110 | 9/1995 | WIPO . |
| 9525721 | 9/1995 | WIPO . |
| 9605175 | 2/1996 | WIPO . |
| 9605818 | 2/1996 | WIPO . |
| 9606606 | 3/1996 | WIPO . |
| 9607405 | 3/1996 | WIPO . |
| 9613492 | 5/1996 | WIPO . |
| 9615099 | 5/1996 | WIPO . |
| 9615100 | 5/1996 | WIPO . |
| 9615108 | 5/1996 | WIPO . |
| 9617832 | 6/1996 | WIPO . |

OTHER PUBLICATIONS

Meyerhoff et al., "Genetically epilepsy–prone rats have increased brain regional activity of an enzyme which liberates glutamate from N–acetyl–aspartyl–glutamate," Brain Research, 593, 1992, 140–143.

Meyerhoff et al., "Activity of NAAG–hydrolyzing enzyme in brain may affect seizure susceptibility in genetically epilepsy–prone rats," Molecular Neurobiology of Epilepsy (Epilepsy Res. Suppl. 9), 1992, Chap. 16, 163–172.

Vornov, J., "Toxic NMDA–Receptor Activation Occurs During Recovery in a Tissue Culture Model of Ischemia," J. Neurochemistry, 1995, 65(4), 1681–1691.

Slusher et al., "NAALADase: A Potential Regulator of Synaptic Glutamate," DuPont NEN Notes, Spring 1994.

Jackson et al., "Design Synthesis, and Biological Activity of a Potent Inhibitor of the Neuropeptidase N–Acetylated α–Linked Acidic Dipeptidase," J. Medicinal Chem., 1995.

Carter et al., "Prostate–specific membrane antigen is a hydrolase with substrate and pharmacologic characteristics of a neuropeptidase," Proc. Natl, Acad, Sci. USA, 1996, vol. 93, 749–753.

Coyle et al., "N–Acetyl–aspartyl Glutamate Recent Developments," Excitatory Amino Acids, 1991, 69–77.

Koening et al., "N–acetyl–aspartyl–glutamate (NAAG) elicits rapid increase in intraneuronal $Ca^{2+}$ in vitro," NeuroReport 5, 1063–1068, 1994.

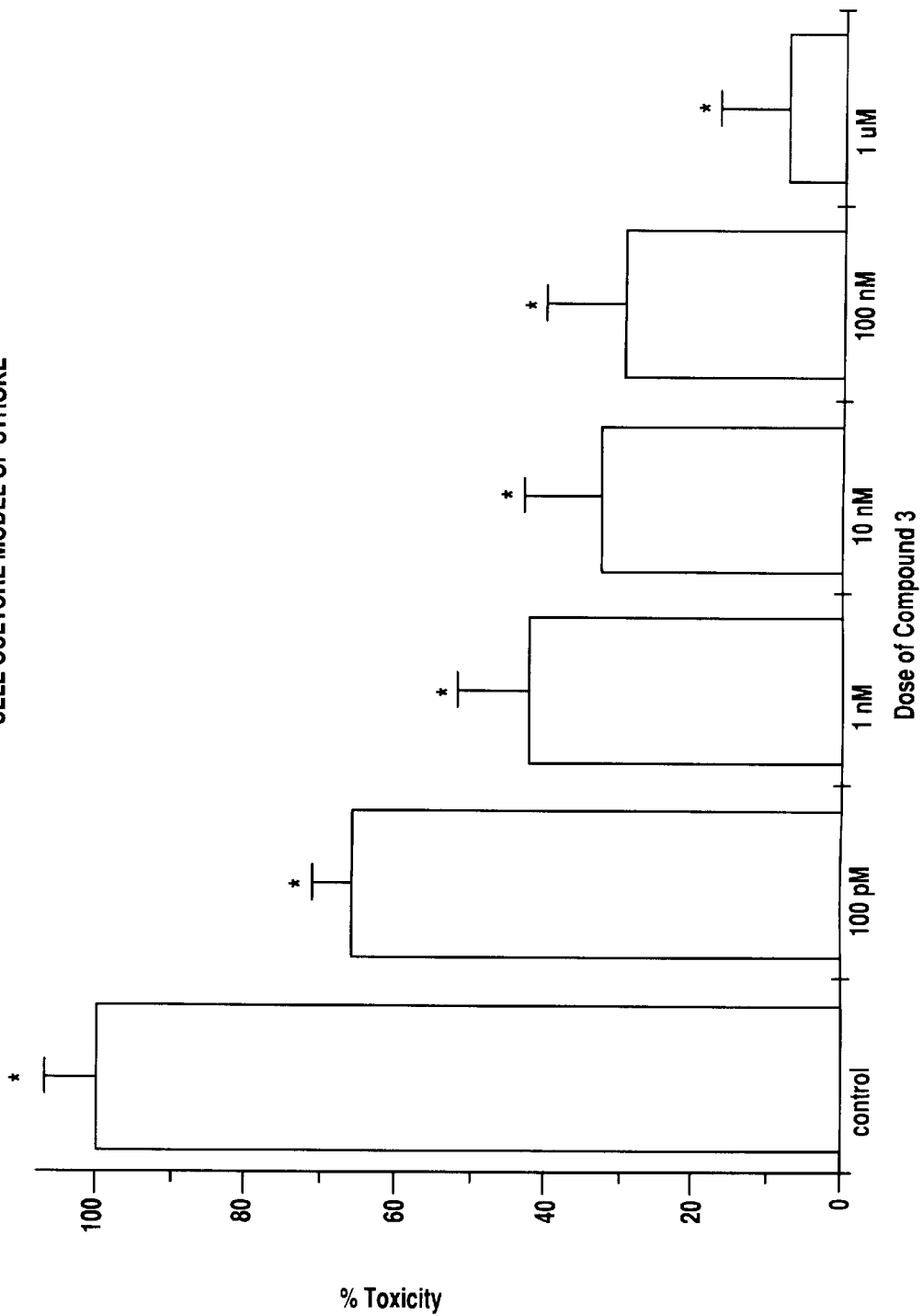
FIG.1 COMPOUND 3 IS NEUROPROTECTIVE IN A CELL CULTURE MODEL OF STROKE

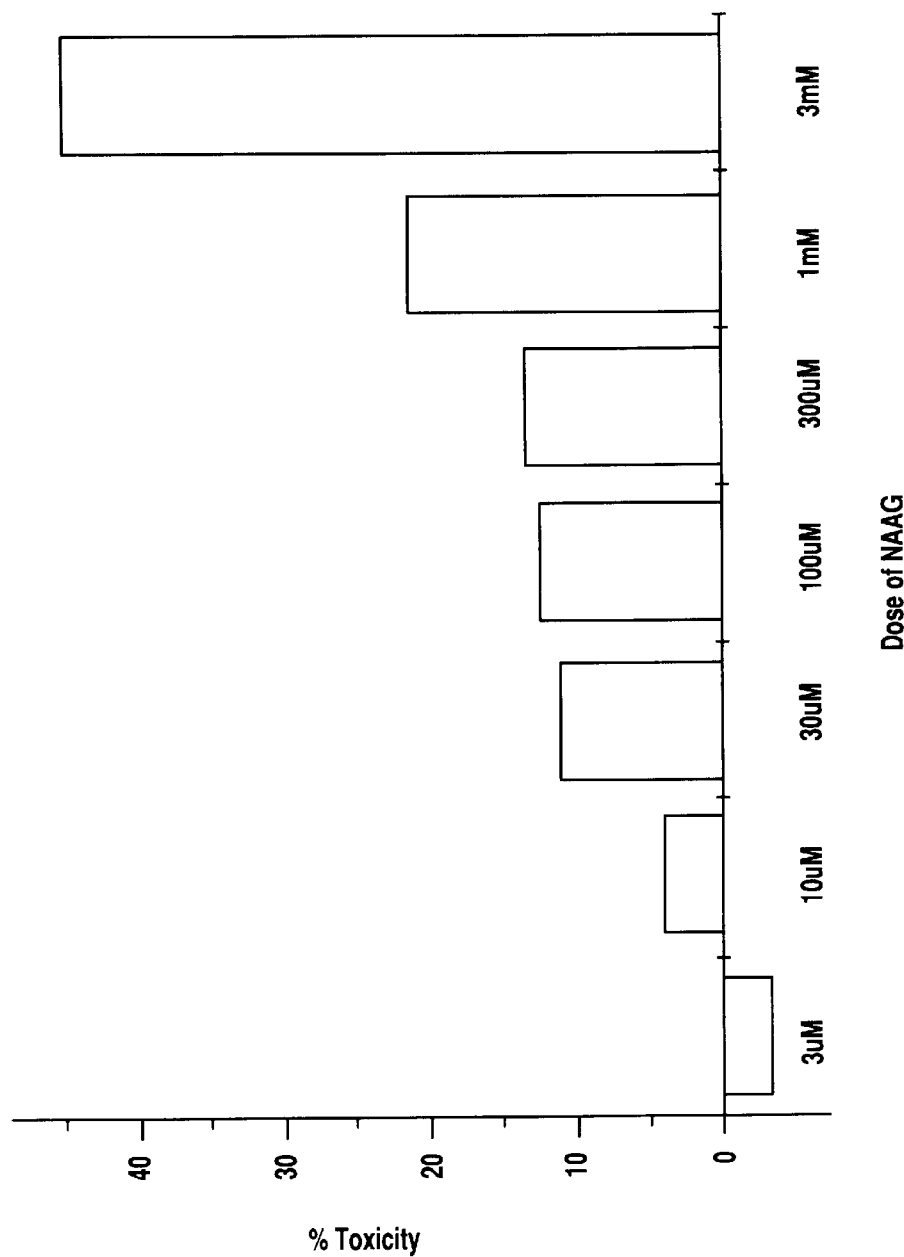

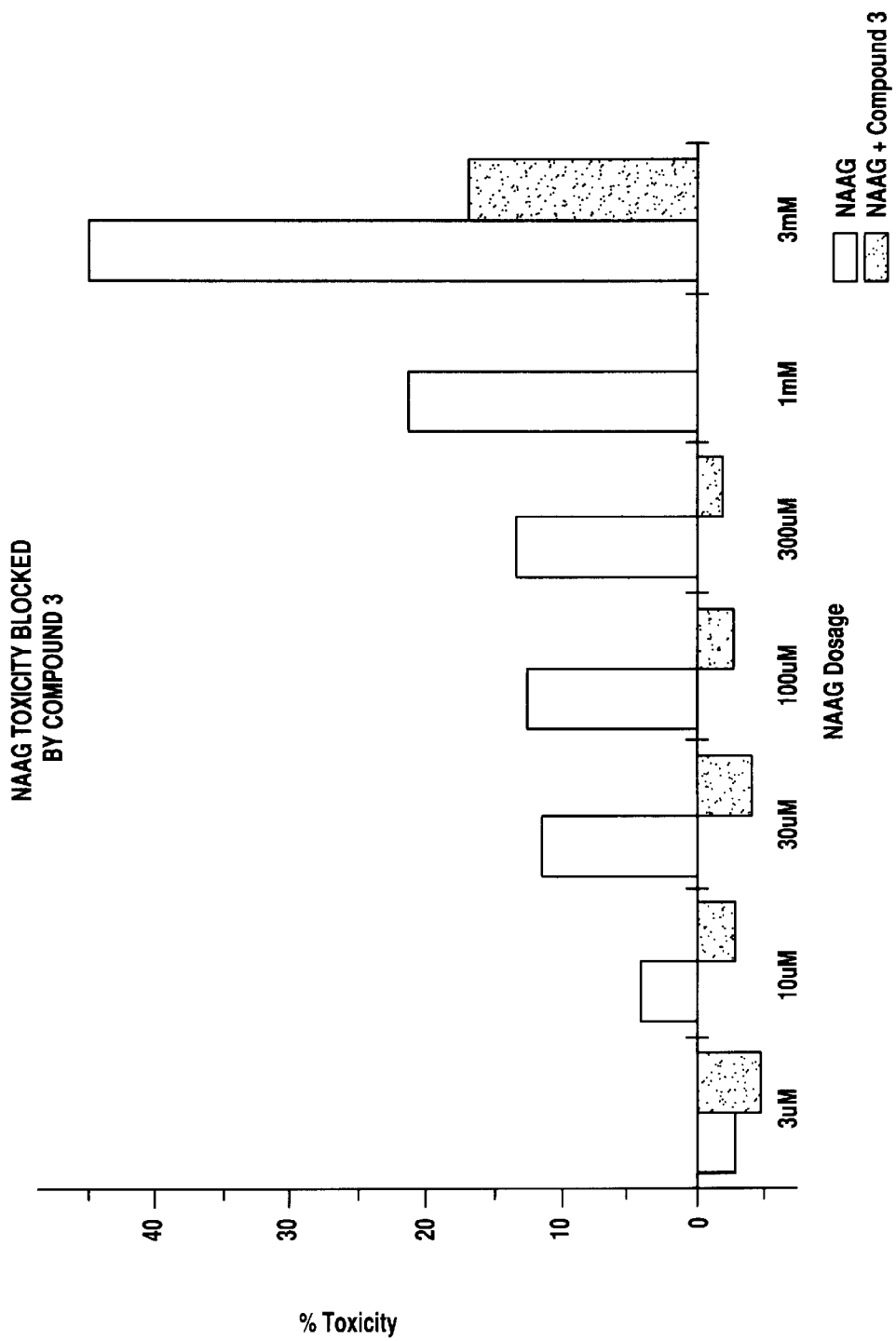

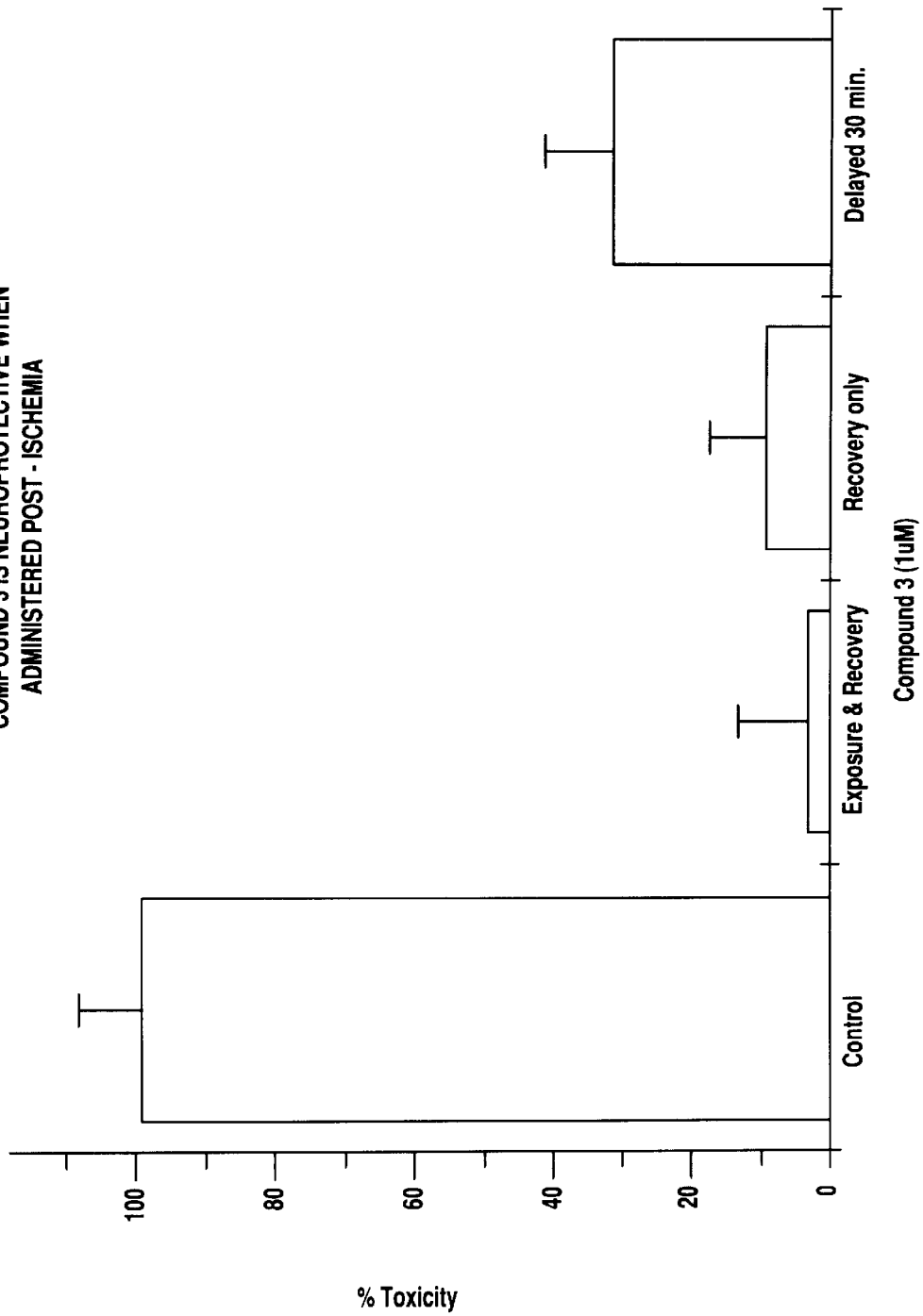

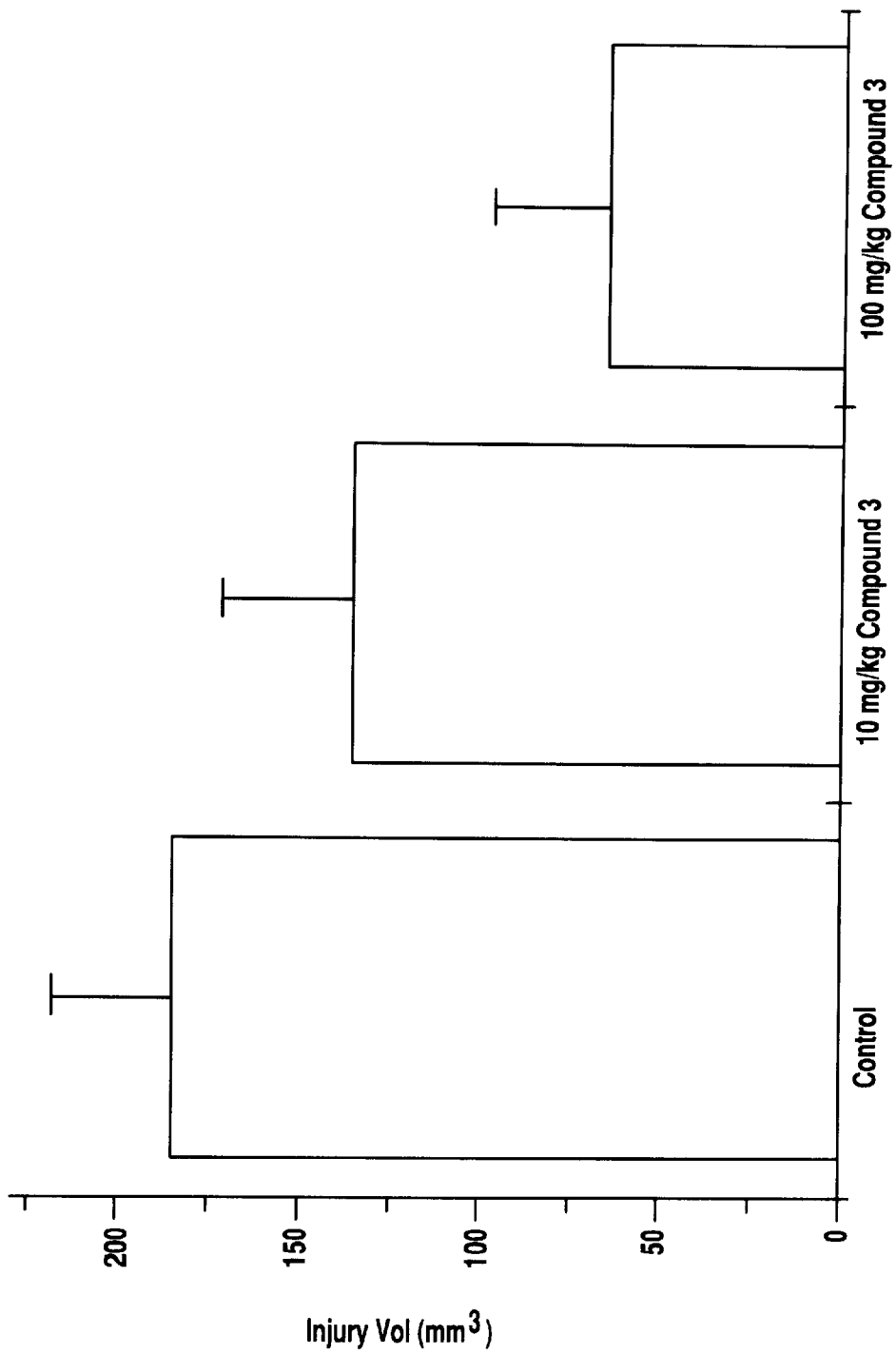

5,824,662

TREATMENT OF GLOBAL AND FOCAL ISCHEMIA USING NAALADASE INHIBITORS

BACKGROUND OF THE INVENTION

1. Field of the Invention

The present invention relates to the treatment of glutamate abnormalities in animals and in particular to the prevention or alleviation of brain damage caused by strokes and other types of ischemia. More particularly, the present invention relates to methods of treating global and focal ischemia before, during and/or after nervous insult has occurred by using compositions which are believed to prevent excess glutamate formation, and which are shown to inhibit N-Acetylated α-Linked Acidic Dipeptidase (NAALADase) enzyme activity in animals.

2. Description of the Prior Art

Ischemia

Ischemia, a localized tissue anemia resulting from the obstruction of the inflow of arterial blood, can cause extensive damage when it occurs in the brain or central nervous system. Central nervous tissue, and to a lesser extent peripheral nervous tissue, has poor reparative abilities. Thus damage to nervous tissue causes significant permanent disability and is a frequent cause of death. Damage to nervous tissue may occur in many ways, not only through ischemia in cerebrovascular accidents, but also in cerebral circulatory disturbances, episodes of absolute and relative hypoxia, from metabolic disturbances and from various forms of trauma.

Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors. In areas of focal ischemia or damage, there is a core of more profound damage, surrounded by a perifocal penumbra of lesser damage. This is because the neurons in the penumbra can for a time maintain homeostasis thus rendering them potentially more salvageable by pharmacological agents.

Both global and focal ischemic conditions have the potential for producing widespread neuronal damage, even if the ischemic condition is transient. Although some permanent neuronal injury may occur in the initial mixture following cessation of blood flow to the brain, the damage in global and focal ischemia occurs over hours or even days following the ischemic onset. Much of this neuronal damage is attributed to glutamate toxicity and secondary consequences of reperfusion of the tissue, such as the release of vasoactive products by damaged endothelium, and the release by the damaged tissues of cytotoxic products including free radicals, leukotrienes, and the like.

Glutamate neurotoxicity, which is a major factor in ischemic neuronal injury, appears to begin with resumption of oxidative metabolism and thus occurs both during reversible ischemia and during recovery. Many attempts have been made to avoid this problem by blocking of the various receptors including NMDA receptors, AMPA receptors, Kainate receptors, and MGR receptors, which are stimulated by glutamate and are also strongly involved in nerve cell death occurring after the onset of global or focal ischemia. When ischemia occurs, such as during a stroke or heart attack, there is an excessive release of endogenous glutamate, resulting in the overstimulation of NMDA receptors, AMPA receptors, Kainate receptors, and MGR receptors. Interaction of the glutamate with these receptors causes the ion channel associated with these receptors to open, allowing a flow of cations across the cell membrane. This flux of ions, particularly $Ca^{2+}$ into the cells, plays an important role in nerve cell death.

Much activity has been undertaken in attempting to prevent glutamate from exciting these receptors. This has proven difficult since these receptors each have many different sites to which the glutamate may bind. Furthermore, many of the compositions that are effective in blocking glutamate from these receptors have also proven in clinical trials to be toxic to the animal that they are administered to.

Currently there is no known effective treatment for nervous tissue damage. At best, supportive measures may be taken in a hospital during the period after nervous tissue insult, such as stroke or trauma. Several drug strategies that have been proposed for treatment of stroke and other neuronal conditions related to ischemia have met with differing and incomplete success as agents to protect the nervous system from damage. Anti-coagulants, such as heparin, have been examined, but with mixed results. Similarly, antivasoconstriction agents, such as flunarazine, excitatory neurotransmitter antagonists, such as MK-801 and AP7, and anti-edemic compounds have shown mixed results, with no clear benefits to outweigh a variety of side effects, including neurotoxicity or increased susceptibility to infection. Nitodipine, a calcium channel blocker, is used clinically to treat vasospasm after subarachnoid hemorrhage. Methylprednisolone, a steroid, in very high doses is helpful in spinal cord compression. Tirilazad, a 21-aminosteroid linked to a free radical scavenger, underwent clinical trials to decrease the damage caused by stroke.

The high rate of disability from nervous insults demonstrates the need for an effective neuroprotective agent. Unfortunately, drugs which have been proposed to date for the treatment of stroke and other ischemic-related conditions of the brain are either (i) relatively ineffective, (ii) effective only at dosage levels where undesired side effects are observed, (iii) produce systemic effects, such as hypotension, which comprise the potential effectiveness of the drug, and/or (iv) are toxic to the patient.

Glutamate toxicity within the Central Nervous System

Efforts to examine the role of glutamate toxicity in diseases of the brain, i.e. epilepsy, amyotrophic lateral sclerosis (ALS), schizophrenia, and Alzheimer's disease, led researchers in an attempt to ascertain the exact role of N-acetylated α-linked acidic dipeptidase (NAALADase) and N-acetyl-L-aspartate-L-glutamate (NAAG) in the central nervous system (CNS).

The dipeptide NAAG is an abundant nervous system specific peptide which is present in synaptic vesicles and released upon neuronal stimulation in several systems. As a major peptidic component of the brain, NAAG is present in levels comparable to that of the major inhibitory neurotransmitter γ-aminobutyric acid (GADA). Although NAAG was first isolated in 1964, there was little activity toward elucidating its role in the CNS until the deleterious nature of excess glutamate in a variety of disease states became apparent. Due to its structural similarity to glutamate, NAAG has been suggested to have a variety of roles similar to those of glutamate itself, including functioning as a neurotransmitter or a cotransmitter, neuromodulator, or as a precursor of the neurotransmitter glutamate. NAAG has elicited excitatory responses both in vitro and in vivo, but is significantly less potent than glutamate.

NAALADase

In 1988, a brain enzyme, NAALADase, was identified which hydrolyzes NAAG to N-acetylaspartate (NAA) and glutamate (See Formula 1).

Catabolism of NAAG by the peptidase NAALADase.

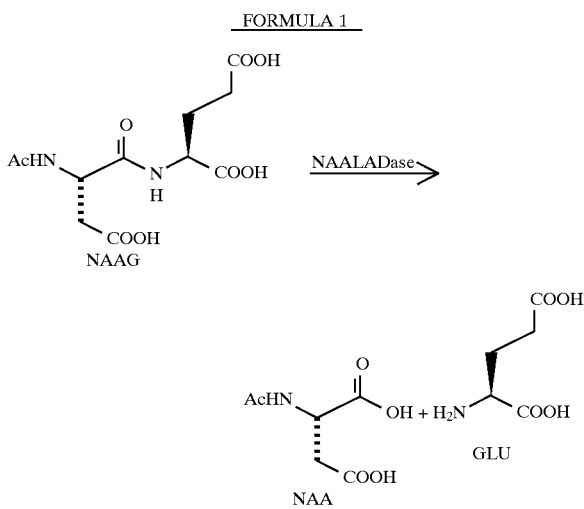

NAALADase, which derives its name from its structural specificity for N-acetylated acidic dipeptides, is a membrane-bound metallopeptidase having a denatured molecular mass of 94 $kDa_x$, that catabolizes NAAG to N-acetylaspartate (NAA) and glutamate. It has been demonstrated that [$^3$H]NAAG is degraded in vivo by an enzyme with the pharmacological characteristics of NAALADase, which supports a role for NAALADase in the metabolism of endogenous NAAG.

Rat NAALADase activity has been extensively characterized and demonstrates a high affinity for hydrolysis of its putative substrate NAAG, with a Km=140 nM. Recently, NAALADase also has been shown to cleave the non-acetylated peptide, aspartylglutamate, with high affinity. Research has also found that the enzyme is membrane-bound, stimulated by chloride ions, and inhibited by polyvalent cation chelators, suggesting that it is a metallopeptidase.

In animals, NAALADase is enriched in synaptic plasma membranes and is primarily localized to neural tissue and the kidneys. NAALADase has not been found in large quantities in the mammalian liver, heart, pancreas, or spleen.

Examination of NAAG and NAALADase has been conducted for several different human and animal pathological conditions. It has been demonstrated that intra-hippocampal injections of NAAG elicit prolonged seizure activity. More recently, it was reported that rats genetically prone to epileptic seizures have a persistent increase in their basal level of NAALADase activity. These observations are consistent with the hypothesis that increased availability of synaptic glutamate elevates seizure susceptibility, and suggest that NAALADase inhibitors may provide anti-epileptic activity.

NAAG and NAALADase have also been implicated in the pathogenesis of ALS and in the pathologically similar animal disease called Hereditary Canine Spinal Muscular Atrophy (HCSMA). It has been shown that concentrations of NAAG and its metabolites—NAA, glutamate and aspartate—are elevated two- to three-fold in the cerebrospinal fluid of ALS patients and HCSMA dogs.

In addition, NAALADase activity is significantly increased (two- to three-fold) in post-mortem spinal cord tissue from ALS patients and HCSMA dogs. Although highly speculative, NAALADase inhibitors may be clinically useful in curbing the progression of ALS if increased metabolism of NAAG is responsible for the alterations of CSF levels of these acidic amino acids and peptides. Abnormalities in NAAG levels and NAALADase activity have also been documented in post-mortem schizophrenic brain, specifically in the prefrontal and limbic brain regions, underscoring the importance of examining the metabolism of NAAG in the pathophysiology of schizophrenia.

The identification and purification of NAALADase led to the proposal of another role for NAAG: specifically that the dipeptide may serve as a storage form of synaptic glutamate.

NAALADase Inhibitors

Only a few NAALADase inhibitors have been identified and those that have been identified have only been used in non-clinical neurological research. Examples of such inhibitors include general metallopeptidase inhibitors such as o-phenanthrolene, metal chelators such as EGTA and EDTA, and peptide analogs such as quisqualic acid and beta-NAAG. It should be noted that prior to the compositions of the present invention, NAALADase inhibitors have either had toxic side effects or were not capable of being administered in pharmaceutically effective amounts.

SUMMARY OF THE INVENTION

The present invention is believed to be based upon the surprising discovery that NAALADase inhibitors may prevent the excess formation of glutamate following nervous tissue insult in an animal. Further, the compositions and methods of the present invention provide for the prevention and/or decrease of the irreparable brain and nervous tissue damage or injury including that caused by global ischemia, focal ischemia, and neuronal cell ischemia associated with spinal injuries, stroke, cardiac arrest, head trauma, or drowning using NAALADase inhibitors. The method of the present invention comprises administering to an animal a therapeutically effective amount of a composition which prevents excess glutamate formation, such as by inhibiting N-Acetylated α-Linked Acidic Dipeptidase (NAALADase) enzyme activity in animals. Suitable compositions include glutamate-derived hydroxyphosphinyl derivative compounds, acidic peptide analogs and mixtures thereof.

NAALADase is an enzyme which is a membrane-bound metalloprotease that hydrolyzes the dipeptide, N-acetyl-L-aspartate-L-glutamate (NAAG) to yield glutamate and N-acetylaspartate. The compositions and methods of the present invention are directed to compositions containing phosphinic acid derivatives that inhibit NAALADase enzyme activity and their use for treating glutamate abnormalities such as created by global and focal ischemia.

Preferred compositions and methods of the present invention include a pharmaceutical composition for treating glutamate abnormalities in an animal which comprises an effective amount of a NAALADase inhibitor and a pharmaceutically acceptable carrier and its administration to a patient suffering from diseases associated with glutamate abnormalities.

Other preferred compositions and methods of the present invention include a pharmaceutical composition for treating ischemia which comprises a NAALADase inhibitor and pharmaceutically acceptable carrier for said NAALADase inhibitor and its administration to a patient suffering from ischemia.

Additional preferred compositions and methods of the present invention include a pharmaceutical composition for treating ischemia in an animal which comprises an effective amount of a glutamate modulator and a pharmaceutically acceptable carrier, wherein administration of said glutamate modulator provides at least 65% recovery of tissues after an ischemic event, and more preferably at least 80% recovery of tissues after an ischemic event.

Another preferred method of the present invention is directed to a pharmaceutical composition and method of decreasing injury caused by ischemia which comprises a NAALADase inhibitor and a carrier for effective therapeutic administration of said NAALADase inhibitor and its administration to an animal suffering from a ischemia. In preferred embodiments, the type of ischemia being treated is a brain injury caused by global ischemia.

Another preferred embodiment of the present invention pertains to a composition and method for treating focal ischemia in an animal which comprises a NAALADase inhibitor and a carrier and administration to the location of the focal ischemia an effective therapeutic amount of said pharmaceutical composition.

Another preferred composition and method of the present invention includes a composition and a method for administering the same for treating ischemia which comprises the step of administering to an animal suffering from a ischemia a compound and pharmaceutically acceptable carrier for said compound, the compound having the following formula:

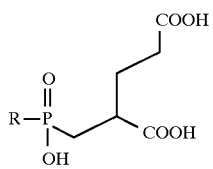

where
R is a $C_1$–$C_9$ straight or branched chain alkyl or alkenyl group, $C_3$–$C_8$ cycloalkyl, $C_3$ or $C_5$ cycloalkyl, $C_5$–$C_7$ cycloalkenyl, $Ar_1$, substituted or unsubstituted $C_1$ alkyl having a carboxy, substituted or unsubstituted $C_3$–$C_9$ alkyl having a carboxy, or substituted $C_2$ alkyl having a carboxy, or pharmaceutically acceptable salts or hydrates thereof.

The present invention also contemplates the use of said alkyl, alkenyl, cycloalkyl, cycloalkenyl, or aryl groups to be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, hydroxy, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or $Ar_1$, and where $Ar_1$ is selected from the group consisting of 1-napthyl, 2-napthyl, 2-indolyl, 3-indolyl, 2-furyl, 3-furyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino; or pharmaceutically acceptable salts or hydrates thereof.

Especially preferred compounds used in the methods of the present invention are selected from the group consisting of:
2-[[methylhydroxyphosphinyl]methyl]pentanedioic acid;
2-[[ethylhydroxyphosphinyl]methlyl]pentanedioic acid;
2-[[propylhydroxyphosphinyl]methyl]pentanedioic acid;
2-[[butylhydroxyphosphinyl]methyl]pentanedioic acid;
2-[[cyclohexylhydroxyphosphinyl]methyl]pentanedioic acid;
2-[[phenylhydroxyphosphinyl]methyl]pentanedioic acid;
2-[[2-(tetrahydrofuranyl)hydroxyphosphinyl]methyl]pentanedioic acid;
2-[[(2-tetrahydropyranyl)hydroxyphosphinyl]methyl]pentanedioic acid;
2-[[((4-pyridyl)methyl)hydroxyphosphinyl]methyl]pentanedioic acid;
2-[[((2-pyridyl)methyl)hydroxyphosphinyl]methyl]pentanedioic acid;
2-[[(phenylmethyl)hydroxyphosphinyl]methyl]pentanedioic acid;
2-[[((2-phenylethyl)methyl)hydroxyphosphinyl]methyl]pentanedioic acid;
2-[[((3-phenylpropyl)methyl)hydroxyphosphinyl]methyl]pentanedioic acid;
2-[[((3-phenylbutyl)methyl)hydroxyphosphinyl]methyl]pentanedioic acid;
2-[[((2-phenylbutyl)methyl)hydroxyphosphinyl]methyl]pentanedioic acid;
2-[[(4-phenylbutyl)hydroxyphosphinyl]methyl]pentanedioic acid; and
2-[[(aminomethyl)hydroxyphosphinyl]methyl]pentanedioic acid.

Highly preferred compounds used in methods of the present invention are selected from the group consisting of:
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid; and 2-[[phenylhydroxyphosphinyl]methyl]pentanedioic acid.

Compositions which are used in methods within the scope of the present invention contain the above described compounds and are formulated with a suitable pharmaceutical carrier. Such carriers are formulated in order to best utilize the compound for a particular purpose.

Yet another preferred embodiment is directed to methods which contain glutamate-derived hydroxyphosphinyl derivatives selected from the group consisting of:
2-(phosphonomethyl)pentanedioic acid;
2-(phosphonomethyl)succinic acid; and,
2-[[(2-carboxyethyl)hydroxyphosphinoyl]methyl]pentanedioic acid.

Further preferred embodiments include the use of additional therapeutic agents useful for treating ischemia. The agent can also include any pharmaceutical compound useful for the treatments described herein to be delivered in combination with the compounds and compositions of the present invention.

Especially preferred NAALADase inhibitors considered to be within the scope of the present methods include glutamate-derived hydroxyphosphinyl derivative compounds. Other preferred NAALADase inhibitors considered within the scope of the present methods include: other metallopeptidase inhibitors such a small molecule compounds with thio derivative functional groups or hydroxamic acid functional group groups; metal chelators such as compounds having the inhibitory characteristics of ethylenediaminetetraacetic acid (EDTA) and ethyleneglycol-bis(beta-aminoethyl ether)-N,N-tetraacetic (EGTA); peptide analogs including aspartate-glutamate (Asp-Glu), glutamate-glutamate (Glu-Glu), glycine-glutamate (Gly-Glu), gamma-glutamate-glutamate (gamma-Glu-Glu), and glutamate-glutamate-glutamate (Glu-Glu-Glu), conformationally restricted glutamate mimics such as quisqualic acid and beta-NAAG, and mixtures thereof.

BRIEF DESCRIPTION OF THE FIGURES

FIG. 1 is a bar graph plotting the in vitro toxicity of ischemic insult (cyanide and 2 deoxy glucose) measured in cortical cultures in the presence of various dosages of Compound 3.

FIG. 2 is a bar graph plotting in vitro toxicity of various doses of NAAG in cortical cultures.

FIG. 3 is a bar graph plotting in vitro NAAG toxicity in cortical cultures blocked by various dosages of Compound 3.

FIG. 4 is a bar graph plotting in vitro toxicity of an ischemic event in cortical cultures in the presence of Compound 3 administered at different times of exposure to the ischemic event.

FIG. 5 is a bar graph plotting the in vivo cortical injury volume in rats following middle cerebral artery occlusion in which various dosages of Compound 3 were administered during the ischemia and for one hour during reperfusion.

DETAILED DESCRIPTION OF THE INVENTION

The present disclosure relates to methods of treating ischemia, in particular global and focal ischemia, using compositions which inhibit N-Acetylated α-Linked Acidic Dipeptidase (NAALADase) enzyme activity in humans and warm-blooded animals.

NAALADase is an enzyme which is a membrane-bound metalloprotease that hydrolyzes the dipeptide, N-acetyl-L-aspartate-L-glutamate (NAAG) to yield glutamate and N-acetylaspartate. The methods of the present invention include using compositions containing phosphinic acid derivatives that inhibit NAALADase enzyme activity and which have been found useful for the treatment of ischemia.

The amino acid L-glutamate is a neurotransmitter that mediates fast neuronal excitation in a majority of synapses in the central nervous system (CNS). Once released into the synapse, L-glutamate can stimulate the N-methyl-D-aspartate (NMDA) receptor, a subtype of an excitatory amino acid receptor. It has been discovered that excessive activation of the NMDA receptor has been implicated in a variety of acute as well as chronic neuropatholgical processes such as ischemia, epilepsy and Huntington's disease. Thus, considerable effort has focused on finding novel therapeutic agents to antagonize the postsynaptic effects of L-glutamate medicated through the NMDA receptor.

Preferred methods of the present invention include a method for treating ischemia which comprises the step of administering to an animal suffering from an ischemia a NAALADase inhibitor and pharmaceutically acceptable carrier for said NAALADase inhibitor.

Especially preferred NAALADase inhibitors considered to be within the scope of the present methods include glutamate-derived hydroxyphosphinyl derivative compounds.

Preferred glutamate-derived hydroxyphosphinyl derivatives include compounds having the following formula:

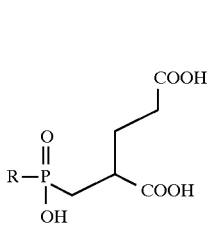

where
R is a $C_1$–$C_9$ straight or branched chain alkyl or alkenyl group, $C_3$–$C_8$ cycloalkyl, $C_3$ or $C_5$ cycloalkyl, $C_5$–$C_7$ cycloalkenyl, $Ar_1$, substituted or unsubstituted $C_1$ alkyl having a carboxy, substituted or unsubstituted $C_3$–$C_9$ alkyl having a carboxy, or substituted $C_2$ alkyl having a carboxy, or pharmaceutically acceptable salts or hydrates thereof.

The present invention also contemplates the use of said alkyl, alkenyl, cycloalkyl, cycloalkenyl, or aryl groups to be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, hydroxy, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or $Ar_1$, and where $Ar_1$ is selected from the group consisting of 1-napthyl, 2-napthyl, 2-indolyl, 3-indolyl, 2-furyl, 3-furyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_3$–$C_4$ alkoxy or $C_1$–$C_4$ alkenyloxy, phenoxy, benzyloxy, and amino; or pharmaceutically acceptable salts or hydrates thereof.

It has been unexpectedly found that the right hand side of the molecular structure depicted above is necessary for substrate recognition by NAALADase enzyme. Thus, the present invention only contemplates substitutions to the left hand side, indicated by the R group, of the phosphinic acid structure above.

"NAALADase" as used herein refers to N-Acetylated Alpha-Linked Acidic Dipeptidase. The enzyme was originally named for it's substrate specificity for hydrolyzing N-acetylated alpha-linked acidic dipeptides. Currently, it is known that the enzyme has a broader range of substrate specificity than originally discovered, particularly that the enzyme does not require N-acetylation or alpha-linkage. Thus, as used herein "NAALADase" encompasses other names used in the literature such as NAAG hydrolyzing enzyme and NAALA dipeptidase.

As used in the specification and claims, the chemical structures refer to conventional designations. For example, "alkyl" is a paraffinic hydrocarbon group which may be derived from an alkane by dropping one hydrogen from the formula, such as methyl, ethyl, propyl, isopropyl, butyl, and so forth. "Alkenyl" is an olefinic unsaturated hydrocarbon having one or more double bonds such as methylene, ethylene, propylene, isopropylene, butylene, and so forth. The term "Cyclo", used herein as a prefix, refers to a structure characterized by a closed ring. The term "oxy", used herein as a suffix, i.e. alkoxy, alkenoxy, phenoxy, and so forth, refers to having one or more oxygen molecules attached. Thus, the term "carboxy" may describe, for example, a carbon having both an oxygen and a hydroxy moiety attached.

"Halogen" includes bromo, fluoro, chloro and iodo; "halomethyl" includes mono-, di-, and tri-halo groups including trifluoromethyl; amino compounds include amine ($NH_2$) as well as substituted amino groups comprising alkyls of one through six carbons; "Ar$^1$", chemical shorthand for "aryl", includes aromatic ring compounds such as benzene, phenyl, naphthyl, indolyl, furyl, thienyl, pyridyl, and substituted forms thereof; "aralkyl" is an aryl being attached through an alkyl chain, straight or branched, of from one through six carbons such as phenylpropyl group.

The term "inhibition", in the context of enzyme inhibition, relates to reversible enzyme inhibition such as competitive, uncompetitive, and noncompetitive inhibition. This can be experimentally distinguished by the effects of the inhibitor on the reaction kinetics of the enzyme, which may be analyzed in terms of the basic Michaelis-Menten rate equation. Competitive inhibition occurs when the inhibitor can combine with the free enzyme in such a way that it competes with the normal substrate for binding at the active site. A competitive inhibitor reacts reversibly with the enzyme to form an enzyme-inhibitor complex [EI], analogous to the enzyme-substrate complex:

$$E + I = EI$$

Following the Michaelis-Menten formalism, we can define the inhibitor constant, $K_i$, as the dissociation constant of the enzyme-inhibitor complex:

$$K_i = \frac{[E][I]}{[EI]}$$

Thus, in accordance with the above and as used herein, $K_i$ is essentially a measurement of affinity between a molecule, and its receptor, or in relation to the present invention, between the present inventive compounds and the enzyme to be inhibited. It should be noted that IC50 is a related term used when defining the concentration or amount of a compound which is required to cause a 50% inhibition of the target enzyme.

The term "ischemia" relates to localized tissue anemia due to obstruction of the inflow of arterial blood. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors.

The term "nervous tissue" refers to the various components that make up the nervous system including neurons, neural support cells, glia, Schwann cells, vasculature contained within and supplying these structures, the central nervous system, the brain, the brain stem, the spinal cord, the junction of the central nervous system with the peripheral nervous sytem, the peripheral nervous system and allied structures.

The term "nervous function" refers to the various functions of the nervous system and its parts which are manifest in sensing the environment, awareness of it, homeostasis to it and interaction with it as shown, by example, in the ability to perform activities of daily living, work, cogitation and speech.

The term "nervous insults" refers to damage to nervous tissue which includes brain and nervous tissue damage and destruction, in whole or in part, and resultant morbidity, disability, neurologic deficia and death. Nervous insult can be from various origins including ischemia, hypoxia, cerebrovascular accident, metabolic, toxic, neurotoxic, trauma, surgery, iatrogenic, pressure, mass effect, hemorrhage, thermal, chemical, radiation, vasospasm, neurodegenerative disease, neurodegenerative process, infection, Parkinson's disease, amyotrophic lateral sclerosis, myelination/demyelination processes, epilepsy, cognitive disorders, glutamate abnormalities, and their secondary effects.

The term "glutamate abnormalities" refers to any condition, disease, or disorder that involves glutamate, and includes but is not limited to the nervous insults listed above.

The term "glutamate modulator" refers to any composition of matter, alone or in combination with another agent, which affects the level of glutamate in an animal, including a human being.

The term "neuroprotective" is an effect which reduces, arrests, or ameliorates nervous insult and is protective, resuscitative or revivative for nervous tissue that has suffered nervous insult.

The term "treatment" refers to any process, action, application, therapy, or the like, wherein an animal, including a human being, is subject to medical aid with the object of improving the animal's condition, directly or indirectly.

The following chemical compounds are designated according to the following index to faciliate discussion and further referenced in Examples 1, 2, and 3:

"Compound 1" refers to 2-Methylenepentanedioate;
"Compound 2" refers to Dibenzyl 2-[[Bis(benzyloxy) phosphoryl]methyl]-pentanedioate;
"Compound 3" refers to 2-(Phosphonomethyl)pentanedioic Acid.

The method of this invention for treating global ischemia comprises administering internally to a subject expected to be benefitted thereby with an effective amount of a NAALADase inhibitor. Doses of this isomer included in the present methods and pharmaceutical compositions are an efficacious, nontoxic quantity. Persons skilled in the art using routine clinical testing are able to determine optimum doses. The desired dose is administered to a subject from 1 to 6 or more times daily, orally, rectally, parenterally, or topically and may follow a higher initial amount administered as a bolus dose.

In methods of treating stroke, particularly acute ischemic stroke, and global ischemia caused by drowning, head trauma and so forth, a NAALADase inhibitor can be co-administered with one or more agents active in reducing the risk of stroke, such as aspirin or ticlopidine (preferably ticlopidine, which has been demonstrated to reduce the risk of a second ischemic event). Co-administration can be in the form of a single formulation (combining, for example, a NAALADase inhibitor and ticlopidine with pharmaceutically acceptable excipients, optionally segregating the two active ingredients in different excipient mixtures designed to independently control their respective release rates and durations) or by independent administration of separate formulations containing the active agents.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a. pharmaceutical composition which comprises a pharmaceutical excipient in combination with a NAALADase inhibitor. The level of the drug in a formulation can vary within the full range employed by those skilled in the art, namely, from about 0.01 percent weight (% w) to about 99.99% w of the drug based on the total formulation and about 0.01% w to 99.99% w excipient. Preferably, the formulation will be about 3.5 to 60% by weight of the NAALADase inhibitor, with the rest being suitable pharmaceutically excipients.

Since there is substantial evidence that NAALADase is a metallopeptidase, the present invention includes small molecules with functional groups known to inhibit metallopeptidases, such as hydroxyphosphinyl derivatives, thio derivatives, and hydroxamic acids. The most preferred methods of the present invention are those that utilize hydroxyphosphinyl derivatives. In particular, since it was known in neurological literature that the glutamate moiety of NAAG was important for recognition by the enzyme and that the aspartate region played a less critical role, a series of glutamate-derived hydroxyphosphinyl derivatives were produced.

As a result, it has been unexpectedly found that compounds with the following general structure were found to be very potent inhibitors of the NAALADase:

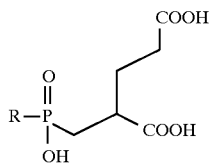

These compounds may be prepared by the general method of Jackson et al. (*J. Med. Chem.* 39(2), 619–622; *J. Med. Chem.* 38, 3313–3331). Their synthesis is outlined in Schemes 1, 2, and 3, below.

Synthesis of NAALADase Inhibitors

All of the above-described inhibitors can be synthesized by standard organic synthetic procedures. The precursor compounds of the present invention can be easily made by a ordinary person skill in the art utilizing known methods, such as Scheme I below. Production of compounds containing the R group substitutions can be easily made utilizing known methods. See, for example, Froestl et al., J. Med. Chem., 1995, 38, 3313–3331, *Phosphinic Acid Analogues of GABA*.

Scheme 1

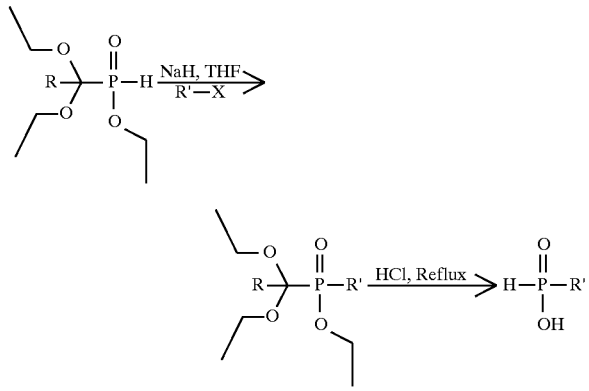

Further methods of synthesizing phosphinic acid esters are also described in *J. Med. Chem.*, 1988, 31, 204–212, and may be found in Scheme II, below.

SCHEME II

Method A

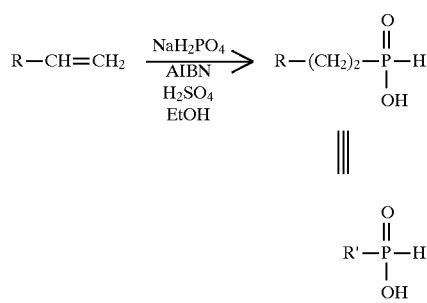

A. R' = (CH$_2$)$_3$Ph     H. n-C$_7$H$_{15}$
B.      (CH$_2$)$_4$Ph     I. n-C$_8$H$_{17}$
C.      (CH$_2$)$_5$Ph     J. n-C$_9$H$_{19}$
D.      (CH$_2$)$_4$(P—F—Ph)  K. n-C$_{10}$H$_{21}$
E.      (CH$_2$)$_4$-(3-pyridyl)  L. CH$_2$(CH)(CH$_3$)C$_4$H$_9$
F.      n-C$_5$H$_{11}$    M. CH$_2$(CH$_3$)CH(CH$_3$)$_2$
G.      n-C$_6$H$_{13}$ Method B

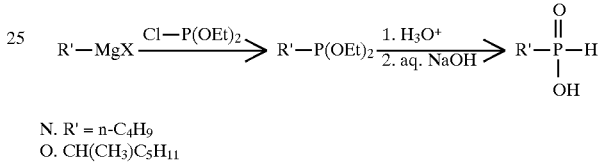

N. R' = n-C$_4$H$_9$
O. CH(CH$_3$)C$_5$H$_{11}$

Starting with the aforementioned phosphinic acid esters, there are a variety of routes that can be used to prepare the compounds of the present invention. For example, a general route set forth below in Scheme III, was recently described in *J. Med. Chem.*, 1996, 39, 619–622.

SCHEME III

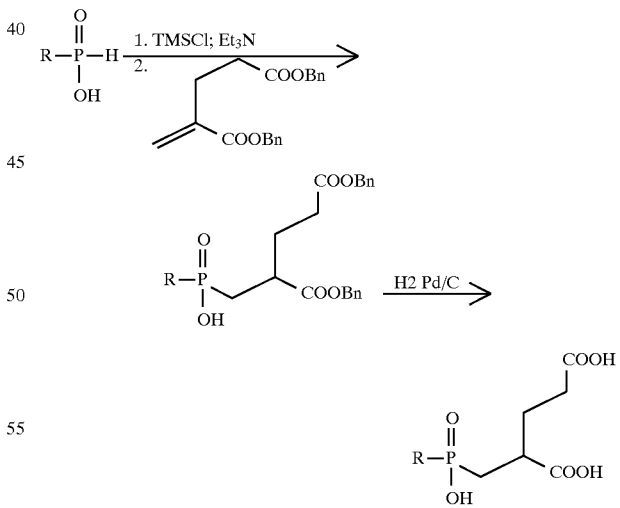

In vitro inhibition of NAALADase Activity

Three compounds were tested for inhibition of NAALADase activity: 2-(phosphonomethyl) pentanedioic acid, 2-(phosphonomethyl)succinic acid, and 2-[[2-carboxyethyl) hydroxyphosphinol]methyl]-pentanedoic acid. The results are shown in Table I.

TABLE I in vitro Activity of NAALADase Inhibitors

| compound | $K_i$ (nM) |
| --- | --- |
| 2-(phosphonomethyl)pentanedioic acid | 0.275 ± 0.08 |
| 2-(phosphonomethyl)succinic acid | 700. ± 67.3 |
| 2-[[2-carboxyethyl)hydroxyphosphinoyl]methyl]-pentanedoic acid) | 1.89 ± 0.19 |

2-(phosphonomethyl)pentanedioic acid showed a high level of NAALADase inhibiting activity, with a $K_i$ of 0.27 nM (Table I). The activity of this compound is >1000 times more potent than that of previously described inhibitors. The procedure for assaying the compounds is set forth below.

NAALADase activity was assayed as described. In brief, the assay measured the amount of [$^3$H]Glu liberated from [$^3$H]NAAG in 50 mM Tris-Cl buffer in 15 min at 37° C. using 30–50 μg of synaptosomal protein; substrate and product were resolved by anion-exchange liquid chromatography. Duplicate assays were always performed so that no more than 20% of the NAAG was digested, representing the linear range of peptidase activity. Quisqualate (100 μM) was included in parallel assay tubes to confirm the specificity of measurements.

The 2-(phosphonomethyl)succinic acid showed a large decrease in efficacy in inhibiting the activity of NAALADase (Table I), suggesting that a glutamate analog attached to the phosphonic acid is required for potent inhibition of the enzyme. In addition, 2-[[2-carboxyethyl)hydroxyphosphinoyl]methyl]-pentanedoic acid, which has an additional carboxylic acid side chain similar to the aspartate residue found in NAAG, did not lead to an increase in potency.

It is believed that the compounds of the present invention will not tend to be particularly toxic when administered to humans in that NAALADase inhibitors have not demonstrated toxic side effects when administered to rats and mice during in vivo neurological experiments. Furthermore, NAALADase inhibitors have not demonstrated toxic side effects upon exposure to cell lines.

In order to explore the potential toxicological effects of NAALADase inhibition, a group of mice were injected with a single peritoneal dose of 2-(phosphonomethyl) pentanedioic acid, a NAALADase inhibitor having a high activity. The dosages were given in increasing concentrations of milligrams (mg) per kilogram (kg) of body weight. Dosages of 1, 5, 10, 30, 100, 300, and 500 mg/kg (of body weight) were administered and no acute adverse effects were observed at any dose tested. The mice were subsequently observed two times per day for 5 consecutive days. Table II gives the percent survival rate for the doses tested.

TABLE II

Non-Toxicity of NAALADase Inhibitor

| | DOSES OF COMPOUND | | | | | | |
| --- | --- | --- | --- | --- | --- | --- | --- |
| mg/kg | 1 | 5 | 10 | 30 | 100 | 300 | 500 |
| % of animal survival as of Day 5 | 100 | 100 | 100 | 100 | 100 | 100 | 66.7 |

The compounds of the present invention can be used in the form of salts-derived from inorganic or organic acids and bases. Included among such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemissulfate heptanoate, hexanoate, hydrochloride, hydrobromide, hydroiodide, 2-hydroxyethanesulfonate, lactate, maleate, methanesulfonate, 2-naphthalensulfonate, nicotinate, oxalate, pamoate, pectinate, propionate, succinate, tartrate, thiocyanate, tosylate and undecanoate. Ease salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

ROUTE OF ADMINISTRATION

For these purposes, the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques. Generally, at the present time, invasive techniques are preferred, articularly administration directly into tumors.

In addition, administration may be by a single dose, it may be repeated at intervals or it may be by continuous infusion. Where continuous infusion is preferred, pump means often will be particularly preferred for administration. Especially, subcutaneous pump means may be preferred in this regards.

Since NAALADase inhibitors are small, easily diffusible, and relatively stable, it is well suited to long-term continuous administration, such as by a perfusion pump. Also, it may be desirable to administer NAALADase inhibitors and other agents of the present invention by intraperitoneal injection on a regular basis.

Compositions and methods of the invention also may utilize controlled release technology. Thus, for example, NAALADase inhibitors may be incorporated into a hydrophobic polymer matrix for controlled release over a period of days. Such controlled release films are well known to the art. Examples of polymers commonly employed for this purpose that may be used in the present invention include nondegradable ethylene-vinyl acetate copolymer and degradable lactic acid-glycolic acid copolymers. Certain hydrogels such as poly(hydroxyethylmethacrylate) or poly (vinylalcohol) also may be useful, but for shorter release cycles then the other polymer releases systems, such as those mentioned above.

To be effective therapeutically in instances where the central nervous system is being treated, the composition should be formulated such that it will readily penetrate the blood-brain barrier in effective amounts when peripherally administered. Accordingly, compositions will be administered having an appropriate polarity, size, characteristic, or additional agent or condition to ensure adminstration to the target cells or tissues. However, for compositions which are administered locally, such by injection or by polymeric implant, such neurological concerns may be obviated.

The pharmaceutical compositions may be in the form of a sterile injectable preparation, for example as a sterile injectable aqueous or oleaginous suspension. This suspension may be formulated according to techniques know in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. Fatty acids such as oleic acid and its glyceride derivatives find use in the preparation of injectables, olive oil or castor oil, especially in their polyoxyethylated versions. These oil solutions or suspensions may also contain a long-chain alcohol diluent or dispersant.

The compounds of the present invention may be administered to the brain by intra-arterial injection or infusion into cerebral artery leading to the brain.

Optionally, an agent to open the blood-brain barrier may be administered before, after or with the compounds of the present invention. They may also be administered via venous route, while the drug or agent to open the blood-brain barrier could be administered by arterial route.

The compounds may be administered orally in the form of capsules or tablets, for example, or as an aqueous suspension or solution. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at rectal temperature and therefore will melt in the rectum to release the drug. Such materials include cocoa butter, beeswax and polyethylene glycols.

The compounds of this invention may also be administered optically, especially when the conditions addressed for treatment involve areas or organs readily accessible by topical application, including neurological disorders of the eye, the skin, or the lower intestinal tract. Suitable topical formulations are readily prepared for each of these areas. For ophthalmic use, the compounds can be formulated as micronized suspensions in isotonic, pH adjusted sterile saline, or, preferably, as solutions is isotonic, pH adjusted sterile saline, either with or without a preservative such as benzylalkonium chloride. Alternatively for the ophthalmic uses the compounds may be formulated in an ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract may be effected in a rectal suppository formulation, as described above, or in a suitable enema formulation.

The present invention also is direct to the timing and sequence of delivery of treatment medications to include pretreatment. To maximize protection of nervous tissue from nervous insult, the compounds of the present invention should be administered as soon as possible within the affected cells. This would include administration before the nervous ischemic insult in situations of increased likelihood of ischemia or stroke. Known in anticipatory situations of include surgery (cartoid endarterectomy, cardiac, vascular, aortic, orthopedic), endovascular procedures such as any type of arterial catherization (cartoid, vertebral, aortic, cardia, renal, spinal, Adamkiewicz and others) for diagnostic or therapeutic purposes including evaluation and treatment of vascular stenosis, aneurysm or arteriovenous malformation and or injection of embolic agents, coils or balloons for hemostasis, interruption of vascularity or treatment of brain lesions, predisposing medical conditions, including crescendo transient ischemic attacks, anticipated emboli or sequential strokes. Where pretreatment for stroke or ischemia is not possible or practicable, it is important to get the compounds of the present invention to the affected cells as quickly as possible during or after the event. The time between the stroke, diagnosis and treatment should be reduced to its minimum to save the ischemic cells from damage and death.

DOSE

Dosage levels on the order of about 0.1 mg to about 10,000 mg of the active ingredient compound are useful in the treatment of the above conditions, with preferred levels of about 0.1 mg to about 1,000 mg. One preferred embodiment has a dosage level of 100 mg/kg for one-time bolus. Another embodiment has a dosage level of 20 mg/kg per hour continuous over two hours. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular ischemia being treated and form of administration.

Treatment dosages generally may be titrated to optimize safety and efficacy. Typically, dosage-effect relationships from in vitro initially can provide useful guidance on the proper doses for patient administration. Studies in animal models also generally may be used for guidance regarding effective dosages for treatment of ischemia in accordance with the present invention. In terms of treatment protocols, it should be appreciated that the dosage to be administered will depend on several factors, including the particular analog that is administered, the route administered, the condition of the particular patient, etc. In that most of these agents have peptidyl portions it will generally be desirable to administer the agents I.V., but administration by other routes is contemplated where appropriate. Generally speaking, one will desire to administer an amount of the agent that is effective to achieve a serum level commensurate with the concentrations found to be effective in vitro. Thus, where an agent is found to demonstrate in vitro activity at, e.g., 10 μM, one will desire to administer an amount of the drug that is effective to provide about a 10 μM concentration in vivo. Determination of these parameters are well within the skill of the art.

These considerations, as well as effective formulations and administration procedures are well known in the art and are described in standard textbooks.

A particular formulation of the invention uses a lyophilized form of NAALADase inhibitor, in accordance with well known techniques. For instance, 1 to 100 mg of NAALADase inhibitor may be lyophilized in individual vials, together with carrier and buffer compound, for instance, such as mannitol and sodium phosphate. The NAALADase inhibitor may be reconstituted in the vials with bacteriostatic water and then administered, as described elsewhere herein.

ADMINISTRATION REGIMEN

Any effective treatment regimen can be utilized and readily determined and repeated as necessary to effect treatment.

In clinical practice, the compositions containing NAALADase inhibitor alone or in combination with other therapeutic agents are administered in specific cycles until a response is obtained.

COMBINATIONS WITH OTHER ACTIVE AGENTS

According to another aspect of the invention, pharmaceutical compositions of matter useful for treating ischemia are provided that contain, in addition to the aforementioned compounds, one or more additional therapeutic agents active in reducing the risk of stroke, such as aspirin or ticlopidine. Ticlopidine is preferred as it has been demonstrated to reduce the risk of a second ischemic event.

In Vitro Assay of NAALDase Inhibitors on Ischemia

Referring now to FIG. 1 of the drawings, the effect of different doses of Compound 3 on the amount of in vitro toxicity following ischemic insult in cortical cultures is shown. Concentrations ranging from 100 pM to 1 μM of Compound 3 administered during ischemic insult and for one hour following show a sharp decrease in the amount of in vitro toxicity. The percentages concerning the toxicity for different doses is shown graphically in FIG. 1. The numerical percentages are also provided below in Table III.

TABLE III

| Dose | % Toxicity |
|---|---|
| Control | 100. ± 9.0 (n = 5) |
| 100 pM | 66.57 ± 4.38 (n = 5) |
| 1 nM | 42.31 ± 9.34 (n = 5) |
| 10 nM | 33.08 ± 9.62 (n = 5) |

TABLE III-continued

| Dose | % Toxicity |
|---|---|
| 100 nM | 30.23 ± 9.43 (n = 5) |
| 1 uM | 8.56 ± 8.22 (n = 5) |

The methods for obtaining the data shown above in Table III and graphically represented in FIG. 1 are set forth in the protocol described in Example 11, below.

Ischemia was then induced using potassium cyanide and 2-deoxyglucose (2-DG) in a standard technique, such as that described in Example 11, below.

Cultures and media were then assayed according to standard cytologic cell injury assay, such as the LDH Assay set forth and described below in Example 11.

In Vitro Toxicity of NAAG on Cortical Cultures

Referring now to FIG. 2 of the drawings, NAAG toxicity in cortical cell cultures is plotted graphically against various dosages of NAAG. Dosages of NAAG are administered for 20 minutes and range from 3 uM to 3 mM, and include 3 uM, 10 uM, 30 uM, 100 uM, 300 uM, 1 mM, and 3 mM. Numerical results of the percentage toxicity are also shown in Table IV, below.

TABLE IV

| Dose of NAAG | % Toxicity |
|---|---|
| 3 μM | 3.51 (n = 1) |
| 10 μM | 4.3 ± 3.12 (n = 3) |
| 30 μM | 11.40 ± 6.17 (n = 3) |
| 100 μM | 12.66 ± 5.50 (n = 3) |
| 300 μM | 13.50 ± 4.0 (n = 3) |
| 1 mM | 21.46 ± 4.20 (n = 3) |
| 3 mM | 45.11 ± 4.96 (n = 3) |

In Vitro Assay of NAAG Toxicity as Blocked by Compound 3

Referring now to FIG. 3 of the drawings, NAAG toxicity in cortical cell cultures is graphically plotted against NAAG toxicity in the presence of Compound 3 (1 μM). Compound 3 was administered during exposure to NAAG and for one hour following NAAG exposure. Numerical results of the comparative toxicity are also shown in the percentages of Table V. Clearly, comparing the results of FIG. 2/Table IV and FIG. 3/Table V show the remarkable protective effects of the compounds of the present against nervous insult or neuronal damage.

TABLE V

| Dose of NAAG | % Toxicity with Compound 3 |
|---|---|
| 3 μM | -4.71 (n = 1) |
| 10 μM | -3.08 ± 0.81 (n = 3) |
| 30 μM | -4.81 ± 1.13 (n = 3) |
| 100 μM | -2.87 ± 0.78 (n = 3) |
| 300 μM | -2.09 ± 0.48 (n = 3) |
| 1 mM | 0.26 ± 1.11 (n = 3) |
| 3 mM | 16.83 ± 8.76 (n = 3) |

Since NAAG is cleaved by NAALADase to release glutamate, adding NAAG to cortical cultures in the absence of NAALADase inhibitors is shown to be toxic in FIG. 2 (control). FIGS. 2 and 3 show that the addition of NAALA- Dase inhibitors along with NAAG provides protection against glutamate-induced neurotoxicity in vitro.

NAALADASE Inhibitors are Protective when Administered Post-Ischemia in Cortical Cultures Referring now to FIG. 4 of the drawings, ischemic toxicity in cortical cultures is graphically plotted against the time of administration of Compound 3. Compound 3 is administered during the exposure to the ischemic insult and for one hour following (exposure and recovery), for one hour post ischemic insult only (recovery only), and for one hour beginning 30 minutes post ischemic insult (delayed 30 minutes). Remarkable in vitro protective effects are shown not only when the compounds of the present invention are administered during exposure to the ischemic event and during recovery from the ischemic event, but also that significant neuronal protection may be achieved when administration of the compositions of the present invention are delayed 30 minutes. Numerical results of the percentage toxicity are also shown in Table VI.

TABLE VI

| Time of Administration relative to Ischemic Event | % Toxicity |
| --- | --- |
| CONTROL | 100% |
| Exposure & Recovery | 2.54% |
| Recovery Only | 9.03% |
| Delayed 30 minutes | 31.49% |

In Vivo Infarct Volume After Administration

Because the in vitro results using Compound 3 were so strikingly protective against injury from ischemic insult, the in vivo neuroprotection using Compound 3 was then examined.

Referring now to FIG. 5 and to Table VII below, infarct volume measuring injury to the cortex was evaluated in rats following middle cerebral artery occlusion (see Example 12). Control animals received saline, other animals received 10 mg/kg of Compound 3 followed by 2 mg/kg/hr of Compound 3 for 1 hour, and still others received 100 mg/kg of Compound 3 followed by 20 mg/kg/hr of Compound 3 for one hour. Again, in vivo protective effects, as demonstrated by the significantly reduced injury volume are shown when the compounds of the present invention are administered during exposure to the ischemic event. Results of the infarct volume testing, shown graphically in FIG. 5 and numerically below in Table VII, show that in high dose administration of compounds of the present invention significant protection of the cortex may be achieved in vivo.

TABLE VII

| Cortical Injury Volume (mm 3) ± S.E.M. | |
| --- | --- |
| Vehicle | 184.62 ± 33.52 (n = 10) |
| 10 mg/kg Compound 3 | 135 ± 32.18 (n = 10) |
| 100 mg/kg Compound 3 | 65.23 ± 32.18 (n = 10) |
| Cortical Injury Volume (% injury) ± S.E.M. | |
| vehicle | 34.44 ± 6.53 (n = 10) |
| 10 mg/kg Compound 3 | 29.14 ± 7.68 (n = 10) |
| 100 mg/kg Compound 3 | 13.98 ± 6.64 (n = 10) |
| Cortical Protection | |
| Vehicle | 0% |
| 10 mg/kg Compound 3: | 27% |
| 100 mg/kg Compound 3 | 65% |

The following examples are illustrative of preferred embodiments of methods of preparation of compounds of the invention and are not to be construed as limiting the invention thereto. Unless otherwise indicated, all percentages are based upon 100% of the final formulations.

EXAMPLE 1

This example demonstrates the preparation of Dibenzyl 2-Methylenepentanedioate (Compound 1) using Scheme III.

Benzyl acrylate (19.4 g, 120 mmol) was cooled in a two neck 250 ml round bottom flask to approximately 5° C. To this was added dropwise HMPT (2.14 g, 133.1 mmol) at such a rate as to maintain a temperature of 5°–10° C. Once addition was complete the ice/water bath was removed and the mixture allowed to warm to room temperature. Stirring was continued overnight. The clear yellow liquid was added directly to a silica gel column (4 cm*40 cm) and eluted with a gradient (19:1–9:1) solvent system (hexane/EtOAc). The fractions containing the desired material were combined and evaporated to give 1 (10.1 g, 52%) as a clear and colorless liquid. TLC $R_f$ 0.26 (9:1, Hex./EtOAc)

1H-NMR (CDCl3) 7.2–7.3 (m, 10H); 6.15 (s, 1H); 5.55 (s, 1H) ; 5.12 (s, 2H); 5.08 (s,2H); 2.58–2.68 (m, 2H); 2.48–2.55 (m, 2H).

EXAMPLE 2

This example demonstrates the preparation of Dibenzyl 2-[[Bis(benzyloxy)phosphoryl]methyl]-pentanedioate (Compound 2) using Scheme III.

Dibenzyl phosphite (9.5 g, 36 mmol) in 350 ml of dichloromethane was cooled to 0° C. To this stirring solution was added trimethyl aluminum (18.2 ml, 2.0M solution in hexane, 36.4 mmol). After 30 minutes 1 (6.0 g, 37 mmol) in 90 ml of dichloromethane was added dropwise over 10 minutes. The clear and colorless solution was then warmed to room temperature and left to stir overnight. The mixture was then quenched by the slow addition of 5% HCl. After stirring an additional 1.5 hours the lower organic layer was removed and the aqueous layer extracted once with 100ml of dichloromethane. The organics were combined, dried ($MgSO_4$), and evaporated to give a clear light golden liquid. The liquid was chromatographed on silica gel (4 cm*30 cm) and eluted with a gradient (4:1–1:1) solvent system (Hexane/EtOAc). The fractions containing the desired product were combined and evaporated to yield 2 (7.1 g, 42%) as a clear and colorless liquid. The liquid was then distilled on a Kughleror apparatus at 0.5 mm Hg and 195°–200° C. The distillate was discarded and the remaining light golden oil was chromatographed on silica gel (1:1, Hex./EtOAc) to give 2.9 g of 2 as a clear and colorless oil. TLC $R_f$ 0.5 (1:1, Hex./EtOAc)

1H-NMR ($CDCl_3$) 7.1–7.4 (m, 20H); 5.05 (s, 2H); 4.8–5.03 (m, 6H); 2.8 (1H); 2.22–2.40 (m, 3H); 1.80–2.02 (m, 3H).

EXAMPLE 3

This example demonstrates the preparation of 2-(Phosphonomethyl)pentanedioic Acid (Compound 3) using Scheme III.

The benzyl pentanedioate 2(2.9 g, 4.9 mmol) was added to a mixture of 20 ml of methanol containing 0.29 g (6 mol %) of 10% Pd/C. This mixture was hydrogenated on a Parr hydrogenator at 40 psi for 24 hours, filtered and evaporated to give 3(1.0 g, 90%) as a clear slightly golden viscous oil.

1H-NMR ($D_2O$) 2.6–2.78(m, 1H); 2.25–2.40(m, 2H); 1.75–2.15(m, 4H).

EXAMPLE 4

This example demonstrates the preparation of the precursor compound dibenzyl itaconate using Scheme III.

A solution of itaconic acid (1.23 g, 9.45 mmol), triethylamine (18.9 mmol, 1.92 g), and benzyl bromide (23.62 mmol, 4.04 g) in toluene (30 mL) was heated at 80° C. for 16 h. After cooling to room temperature, the solution was diluted with ether (100 mL), washed with 1N hydrochloric acid (20 ML) and water (20 mL), dried (MgSO$_4$), and concentrated. Flash chromatography over silica gel (3×18 cm) with a hexane-EtOAc (20:1–10:1) gradient gave 2b as a clear oil (1.84 g, 63%) TLC R$_f$ 0.28 (9:1 hexanes-EtOAc); $^1$HNMR (300 MHz, CDCl$_3$)α 3.41(s, 2H), 5.09 (s, 2H), 5.17 (s, 2H), 5.73 (s, 1H), 6.39 (s, 1H), 7.23–7.36 (m, 10H); MS (methane, DCI) mlz 311 (M$^+$+1).

EXAMPLE 5

This example demonstrates the preparation of precursor compound dibenzyl 2-[bis(benzyloxy)phosphoryl]methyl]-succinate using Scheme III.

To a solution of dibenzyl phosphite (3.04 g. 11.6 mmol) in THF (20 mL) at 0° C. was added n-butyllithium (11.6 mmol, 4.6 mL, 2.5M solution in hexanes) followed after 10 min by trimethylaluminum (11.6 mmol, 5.8 mL, 2.0M solution in hexanes). After 20 min a solution of 1b (3.0 g, 9.7 mmol) in THF 95 mL) was added. The cooling bath was removed, and the resulting solution stirred at room temperature for 16 h. The reaction was quenched by the slow addition of 1N hydrochloric acid (20 mL). After stirring for 10 min the phases were separated, and the aqueous phase was extracted with ethyl acetate (2×10 mL). The organic phases were combined, dried (MgSO$_4$), and concentrated. Flash chromatography over silica gel (3×18 cm) with a hexane-EtOAc (4:1–1:1) gradient gave 2b as a clear oil (2.6 g, 55%): TLC R$_f$ 0.39 (1:1 hexanes-EtOAc) ; $^1$H NMR (300 MHz, CDCL$_3$) δ2.08 (ddd, J=17.6, 15.5, 8.2 Hz, 1H), 2.35 (ddd, J=19.2, 15.5, 5.5 Hz, 1H), 2.83 (d, J=6.6. Hz, 2H), 3.10–3.27 (m, 1H0, 4.82–5.06 (m, 8H), 7.22–7.37 (m, 20H); MS (methane, DCI) mlz 573 (M$^+$+1). Anal. Calcd for C$_{233}$H$_{33}$O$_7$P: C, 69.22; H, 5.81. Found: C, 69.28; H, 5.86.

EXAMPLE 6

This example demonstrates the preparation of precursor compound 2-(phosphonomethyl) succinic Acid using Scheme III.

The procedure used for the preparation of 3 was followed using 2b (1.4 g, 2.44 mmol) in methanol (10 mL) with 10% palladium on carbon (0.25 g, 5 mol %) to afford 4 (0.55 g). Purification of 4 was carried out by HPLC: semipreparative C$_8$ column, linear gradient of water and methanol (0%–20%) over 20 min, 10 mL fractions. HPLC analysis, Zorbax C$_8$ column, isocratic water-methanol (4:1), showed the product (t$_R$=1.6 min) was contained in fractions 7–10. These fractions were combined and lyophilized to afford 3 (0.44 g, 38%): $^1$H NMR (300 MHz, D$_2$O) δ1.91 (ddd.J= 17.4, 15.5, 7.7 Hz, 1H), 2.13 (dd, J=18.0, 15.5, 6.1 Hz 1H), 2.71–2.92 (m, 2H) 3.01–3.15 (m, 1H); MS (methane, DCI-) mlz 211 (M$^-$1). Anal. Calcd for C$_5$H$_9$O$_7$P.2H$_2$O: C, 24.2; H.5.28. Found: C, 24.2; H, 5.34.

EXAMPLE 7

This example demonstrates the preparation of precursor compound benzyl 3-(hydroxyphosphinyl)propionate using Scheme III.

Hypophosphorous acid (1.82 g, 13.8 mmol, 50% aqueous solution) and triethylamine (0.97 g, 13.8 mmol) were mixed and dried by azeotropic removal of toluene (3×20 mL) in vacuo at 50° C. The residue was dissolved in dry CH$_2$Cl$_2$ (50 mL) and cooled to 0° C. Triethylamine (2.4 g, 24.2 mmol) and chloro-trimethylsilane (2.56 g, 23.6 mmol) were added followed after 5 min by benzyl acrylate (0.32 g, 1.98 mmol) in CH$_2$Cl$_2$ (5 mL). The mixture was stirred for 24 h at room temperature and then filtered. The filtrate was washed with 1N hydrochloric acid (10 mL) and water (10 mL), dried (MgSO$_4$), and concentrated to afford 5 in quantitative yield: $^1$H NMR (300 MHz, CDCL$_3$) δ2.05 (dquintet, J=1.8, 7.7 Hz, 2H), 2.66 (quintet, J=7.7 Hz, 2H), 5.12 (s, 2H), 7.25–7.38 (m, 5H), 10.89 (brs, 1H).

EXAMPLE 8

This example demonstrates the preparation of precursor compound dibenzyl 2[[[2-(benzylcarboxy)ethyl] hydroxyphosphinoyl]methyl]pentanedioate using Scheme II.

Compound 5 (0.82 g, 3.63 mmol) was dried by azeotropic removal of toluene (3×20 mL) in vacuo at 50° C. The residue was dissolved in dry CH$_2$Cl$_2$ (5 mL). The mixture stirred for 24 h at room temperature and then was washed with 1N hydrochloric acid (10 mL) and water (10 mL), dried (MgSO$_4$), and concentrated. Flash chromatography over silica gel (3×18 cm) with a hexane-EtOAc (4:1–1:1) gradient gave 6 as a clear oil (0.74 g 37%): TLC R$_f$0.1 (1:1 hexanes-EtOAc); $^1$H NMR (300 MHz, CDC;$_3$) δ1.70–1.84 (m, 1H), 1.84–2.05 (m, 4H), 2.12–2.35 (m, 3H), 2.51–2.66 (m, 2H), 2.76–2.94 (m, 1H), 5.00–5.17 (m, 6H), 7.20–7.40 (m, 15H); MS (methane, DCI) mlz 553 (M$^-$×1).

EXAMPLE 9

This example demonstrates-the preparation of precursor compound 2-[[2-carboxyethyl)hydroxyphosphinol]methyl] pentanedoic Acid using Scheme II.

The procedure used for the preparation of 3 was followed using 6 (0.58 g, 1.06 mmol) in methanol (10 mL) with 10% palladium on carbon (0.11 g, 10 mol %) to afford 0.31 g of compound 7. Purification of 7 was carried out by HPLC: semipreparative C8 column, linear gradient of water and methanol (0%–20%) over 20 min, 10 mL/min, 20×10 mL fractions. HPLC analysis, Zorbax C8 column, isocratic water-methanol (4:1), showed the product (t$_R$=1.9 min) was contained in fractions 12–15. These fractions were combined and lyophilized to afford 7 (0.17 g, 56%): $^1$H NMR (300 MHZ, MeOD) δ1.82–2.08 (m, 5H), 2.14–2.27 (m, 1H), 2.31–2.43 (m, 2H), 2.51–2.63 (m, 2H), 2.74–2.91 (m, 1H); MS (FAB) mlz 283 (M$^-$).

EXAMPLE 10

This example demonstrates the preparation of precursor compound 2-[[(2-carboxyethyl)hydroxy phosphinoyl] methyl]pentanedioic Acid using Scheme II.

The procedure used for the preparation of 3 was followed using 6 (0.58 g, 1.06 mmol) in methanol (10 mL) with 10% palladium on carbon (0.11 g, 10 mol %) to afford 0.31 g of compound 7. Purification of 7 was carried out by HPLC:semipreparative C$_8$ column, linear gradient of water and methanol (0%–20%) over 20 min, 10 mL/min, 20×10 mL fractions. HPLC analysis, Zorbax C8 column, isocratic water-methanol (4:1), showed the product (t$_R$=1.9 min) was contained in fractions 12–15. These fractions were combined and lyophilized to afford 7 (0.17 g, 56%): $^1$H NMR (300 MHZ, MeOD) δ1.82–2.08 (m, 5H), 2.14–2.27 (m, 1H), 2.31–2.43 (m, 2H), 2.51–2.63 (m, 2H), 2.74–2.91 (m, 1H); MS (FAB) mlz 283 (M$^-$).

EXAMPLE 11

In Vitro Neurotoxicity Assay
a. Cell Culture

Dissociated cortical cultures were prepared using the papain-dissociation method of Heuttner and Baughman (1986) as modified by Murphy and Baraban (1990). See Table VIII for the Dissociated Culture Protocol as used herein. Fetuses of embryonic day 17 were removed from timed pregnancy rats (Harlan Sprague Dawley). The cortex was rapidly dissected out in Dulbecco's phosphate-buffered saline, stripped of meninges, and incubated in a papain solution for 15 min at 37° C. The tissue was then mechanically triturated and pelleted at 500 g (1000–2000 rpm on swinging bucket Beckman). The pellet was resuspended in a DNAase solution, triturated with a 10 mL pipette x15–20, layered over a "10×10" solution containing albumin and trypsin inhibitor (see Table VIII for an example of a "10×10" solution), repelleted, and resuspended in a plating medium containing 10% fetal bovine serum (HyClone A-1111-L), 5% heat-inactivated Equine serum (HyClone A-3311-L), and 84% modified Earle's basal medium (MEM) (Gibco 51200-020) with high glucose (4.5 g/L), and 1 g/L $NaHCO_3$. Each 24-well plate was pretreated with poly-D-lysine (0.5 ml/well of 10 μg/ml) for 1 h and rinsed with water before plating. Cultures were plated at $2.5 \times 10^6$ cells/ml with each well of a 24 well plate receiving 500 μl/well. Alternatively, 35 mm dishes can be plated at 2 mls/dish, 6 well plates at 2 mls/well, or 12 well plates at 1 ml/well. After plating, 50% of the medium was changed every 3–4 days with growth serum containing 5% heat-inactivated Equine serum (HyClone A-3311-L), 95% modified Earle's basal medium (MEM) (Gibco 51200-020), and 1% L-Glutamine (Gibco 25030-081). Experiments were performed after 21 days in cultures. Cultures were maintained in a 5% $CO_2$ atmosphere at 37° C. A detailed description of these methodologies is further described in the table below.

TABLE VIII

DISSOCIATED CULTURE PROTOCOL

I. PREPARE SOLUTIONS
Stocks/Solutions:

| DNAase Stock, 1 mL (100x) | Dulbecco's PBS, 500 mL |
|---|---|
| 5 mgs of DNAase I (Worthington LS002004); 1 ml dissoc. EBSS Freeze as 50 ul aliquots. | 4 gms NaCl (J. T. Baker 3624-01); 1.06 gms $Na_2HPO_4 \cdot 7H_2$) (Fisher S373-3) 100 mg KCl (Fisher P217-500); 100 mg $KH_2PO_4$ (Sigma P-0662); 500 mls $dH_2O$; Adjust pH to 7.4 and sterile filter. |
| Dissociated EBSS, 500 mL | EDTA Stock, 10 mL |
| 1.1 gms $NaHCO_3$; 50 mls EBSS stock (Gibco 14050-025); 450 mls $dH_2O$; Sterile filter. | 184.2 mgs EDTA sodium salt (Sigma ED4S); 10 mls $dH_2O$; Sterile filter. |
| 10 and 10 Stock, 10 mL | Poly-D-Lysine Stock, 5 mL |
| 100 mg BSA (Sigma A-4919); 100 mg Trypsin Inhibitor from Egg White (Sigma T-2011); 10 mls dissoc. EBSS; Sterile filter. Media | 5 mg Poly-D-Lysine, 100–150K (Sigma P-6407); 5 mls sterile water; Keep frozen. |
| Dissociated growth, 500 mL | Plating media, 300 mL |
| 500 mls MEM (Gibco 51200-020) containing glucose and $NaHCO_3$ (2.25 gm glucose and 0.5 gm $NaHCO_3$); 25 mls heat-inactivated Equine Serum (HyClone A-3311-L); 5 mls L-Glutamine (200 mM, 100x stock, Gibco 25030-081); Sterile filter. | 250 mls MEM containing glucose and sodium bicarbonate (2.25 gm glucose and 0.5 gm $NaHCO_3$ in 500 mls Gibco MEM 51200-020); 30 MLS Fetal Bovine Serum (HyClone A-1111-L); 15 mls heat-inactivated Equine Serum (HyClone A-3311-L); 3 mls L-Glutamine (200 mM, 100x stock, Gibco 25030-081); 1 ml Penicillin-Streptomycin stock (Gibco 15140-015); Sterile filter. |
| For papain dissociation: | For DNAase treatment: |
| 4 mg Cysteine (C-8277); 25 mls dissoc. EBSS; 250 μl Papain stock (Worthington LS003126); Place in 37° C. waterbath until clear. | DNAase, 5 mL 4.5 mls dissoc. EBSS; 500 μl "10 and 10" stock; 50 μl DNAase stock. '10 and 10', 5 mL 4.5 mls of EBBS; 500 μl '10 and 10' stock |

II. COAT DISHES

Use poly-d-lysine stock at 1:100 dilution to coat 24-well plates (0.5 ml/well) or at 1:10 dilution to coat 35 mm glass cover slips (1.0 ml/coverslip).
Leave until end of dissection.

III. DISSECT TISSUE

Use Harlan Sprague-Dawley timed pregnancy rats, ordered to arrive at E-17.
Decapitate, spray abdomen down with 70% EtOH.
Remove uterus through midline incision and place in sterile dPBS.
Remove brains from embryos, leaving them in dPBS.
Brain removal: Penetrate skull and skin with fine forceps at lambda.
Pull back to open posterior fossa. Then move forceps anteriorly to separate sagittal suture. Brain can be removed by scooping back from olfactory bulbs under the brain.
Move brains to fresh dPBS; subsequently, dissect away from cortex.

IV. PAPAIN DISSOCIATION

Transfer cortices equally to two 15 ml tubes containing sterile papain solution, maintained at 37° C.
Triturate x1 with sterile 10 ml pipette.
Incubate only for 15 minutes at 37° C.
Spin at 500 G for 5 minutes (1000–2000 RPM on swinging bucket Beckman).

V. DNAase TREATMENT

Remove supernatant and any DNA gel layer from cell pellett (or pick up and remove pellet with pipette).
Move cell pellet to DNAase solution.
Triturate with 10 ml pipette, x15–20.
Layer cell suspension over the '10 and 10' solution by pipetting it against the side of the tubes.
Spin again at 500 G for 5 minutes. (cells with spin into "10 and 10" LAYER).
Wash tube sides with plating media without disturbing pellet.
Pipette off the media wash and repeat the wash.

VI. PLATE

Add about 4.5 mls plating media to each pellet for 5 ml volume.
Re-suspend with 10 ml pipette.
Pool cells into a single tube.
Quickly add 10 μl of the suspended cells to a hemocytometer so that they don't settle.
Count cells per large square, corresponding to 10 million cells/ml.
Put re-suspended cells into a larger container so that they number 2.5 milliion cells/ml. (Thus if there Triturate to homogeneity).
Finish coating plates:
Aspirate or dump Lysine;
Wash x1 with sterile water and dump.
Add plating media, with cells, to the plates as follows:
35 mm dishes    2 mls/dish;
6 well plate    2 mls/well;

TABLE VIII-continued

DISSOCIATED CULTURE PROTOCOL

| | |
|---|---|
| 12 well plate | 1 ml/well; |
| 24 well plate | 500 μl/well. |

VII. FEED

Cultures are usually made on Thursdays
Start feeding twice a week; beginning the following
Monday, feeding Mondays and Fridays.
Remove 50% of volume and replace with fresh growth media.

b. Ischemic Insult using potassium cyanide and 2-deoxyglucose

Twenty-one to twenty-four days following the initial cortical cell plating, the experiment was performed. The cultures were washed three times in HEPES buffered saline solution containing no phosphate. The cultures were then exposed to potassium cyanide (KCN) (5 mM) and 2-deoxyglucose (2-DG) (10 mM) for 20 minutes at 37° C. These concentrations were shown previously to induce maximal toxicity (Vornov et al., J.Neurochem, 1995, Vol. 65, No. 4, pp. 1681–1691). At the end of 24 hours, the cultures were analyzed for release of the cytosolic enzyme lactate dehydrogenase (LDH), a standard measure of cell lysis. LDH measurements were performed according to the method of Koh and Choi (J.Neuroscience Methods, 1987; see example 11).

c. NAAG Induced Neurotoxicity

Cultures were assessed microscopically and those with uniform neuronal densities were used in the NAAG neurotoxicity trials.

At the time of the experiment, the cultures were washed once in HEPES-buffered saline solution (HBSS; NaCl 143.4 mM, HEPES 5 mM, KCl 5.4 mM, $MgSO_4$ 1.2 mM, $NaH_2PO_4$ 1.2 mM, $CaLC_2$ 2.0 mM, D-glucose 10 mM) (Vornov et al., 1995) and then exposed to various concentrations of NAAG for 20 minutes at 37° C. NAAG concentrations ranged from 3 μM to 3 mM, and include 3 μM, 10 μM, 30 μM, 100 μM, 300 μM, 1 mM, and 3 mM. At the end of exposure, the cells were washed once with HEPES buffered saline solution and then replaced with serum free modified Earle's basal medium. The cultures were then returned to the $CO_2$ incubator for 24 hour recovery.

d. Lactate Dehydrogenase Assay

Release of the cytosolic enzyme lactate dehydrogenase (LDH), a standard measure of cell lysis, was used to quantify injury (Koh and Choi, 1987). LDH-activity measurements were normalized to control for variability between culture preparations (Koh et al., 1990). Each independent experiment contained a control condition in which no NAALADase inhibitors were added; a small amount of LDH activity is found in these controls. This control measurement is subtracted from each experimental point. These values were normalized within each experiment as a percentage of the injury caused by NAAG/ischemia. Only main effects of NAALADase inhibitors were considered; interactions between dose and condition were not examined statistically.

A measurement of the potency of each compound tested is made by measuring the percentage of LDH release into the growth media after exposure to NAAG/ischemia plus NAALADase inhibitor or NAAG/ischemia plus saline (control). Since high concentrations of glutamate may be toxic to cells in certain circumstances, measurement of glutamate toxicity is observed using LDH as a standard measurement technique.

EXAMPLE 12

In Vivo Neurotoxicity Assay a. Materials and method

A colony of SHRSP rats was bred at Johns Hopkins School of Medicine from three pairs of male and female rats obtained from the National Institutes of Health (Laboratory, Sciences Section, Veterinary Resources Program, National Center for Research Resources, Bethesda, Md.). All rats were kept in a virus-free environment and maintained on regular diet (NIH 31, Zeigler Bros, Inc.) with water ad libitum. All groups of rats were allowed to eat and drink water until the morning of the experiment.

Transient occlusion of the middle cerebral artery (MCA) was induced by advancing a 4-0 surgical nylon suture into the internal carotid artery (ICA) to block the origin of the MCA (Koizumi, 1986; Longa, 1989; Chen, 1992). Briefly, animals were anesthetized with 4i halothane, and maintained with 1.0 to 1.5% halothane in air enriched oxygen using a 2face mask. Rectal temperature was maintained at 37.0°±0.5° C. throughout the surgical procedure using a heating lamp. The right femoral artery was cannulated for measuring blood gases (pH, oxygen tension [PO2], carbon dioxide tension [PCO2]) before and during ischemia, for monitoring blood pressure during the surgery. The right common carotid artery (CCA) was exposed through a midline incision; a self-retraining retractor was positioned between the digastric and mastoid muscles, and the omohyoid muscle was divided. The right external carotid artery (ECA) was dissected and ligated. The occipital artery branch of the ECA was then isolated and coagulated. Next, the right internal carotid artery (ICA) were isolated until the pterygopalatine artery was exposed, and carefully separated from the adjacent vagus nerve. The pterygopalatine artery was ligated with 4-0 silk suture close to its origin.

After the CCA was ligated with 4-0 silk suture, a 4-0 silk suture to prevent bleeding from a puncture site, through which a 2.5 cm length of 4-0 monofilament nylon suture (Ethilon), its tip rounded by heating near a electric cautery, was introduced into the ICA lumen. A 6-0 silk suture was tightened around the intraluminal nylon suture at the bifurcation to prevent bleeding, and the stretched sutures at the CCA and the ICA were released. The nylon suture was then gently advanced as far as 20 mm.

Anesthesia was terminated after 10 minutes of MCA occlusion in both groups, and animals awoke 5 minutes thereafter. After 2 hours of ischemia, anesthesia was reanesthetized, and reperfusion was performed by withdrawing the intraluminal nylon suture until the distal tip became visible at the origin of the ICA.

Arterial pH and PaCO2, and partial pressure of oxygen (PaO2) were measured with a self-calibrating Radiometer electrode system (ABL 3; Copenhagen, Denmark). Hemoglobin and arterial oxygen content were measured with a hemoximeter (Radiometer, Model OSM3; Copenhagen, Denmark). Blood glucose was measured with a glucose analyzer (model 2300A, Yellow Springs Instruments, Yellow Springs, Ohio).

Each group was exposed to 2 hours of right MCA occlusion and 22 hours of reperfusion. All variables but the rectal temperature were measured at baseline, at 15 minutes and 45 minutes of right MCA occlusion. The rectal temperature were measured at baseline, at 0 and 15 min of MCA occlusion, and at 0 and 22 hours of reperfusion.

FIG. 5 clearly shows that the compounds of the present invention when administered during ischemia significantly reduces injury to the cortex. Thus, significant protection of neurons in vivo may be achieved using the compounds of the present invention.

EXAMPLE 13

A patient is at risk of injury from an ischemic event. The patient would then be pretreated with an effective amount of the compounds of the present invention, such as set forth in examples 1–3. It would be expected that after is the pretreatment the patient would be protected from the injury.

EXAMPLE 14

A patient is suffering from an ischemic event. The patient may then be administered, during the event or within a 30 minute window after such an event, an effective amount of the compounds of the present invention, such as set forth in examples 1–3. It would be expected that the patient would recover or would not suffer significant injury due to the ischemic event.

EXAMPLE 15

A patient has suffered from an ischemic injury. The patient may then be administered an effective amount of the compounds of the present invention, such as set forth in example 1–3. It would be expected that the patient would recover from the ischemic injury.

EXAMPLE 16

A patient is suffering from a disease characterized by glutamate abnormality. The patient may then be administered an effective amount of the compounds of the present invention, such as set forth in example 1–3. It would be expected that the patient would be protected from further injury caused by the glutamate abnormality or would recover from the disease.

EXAMPLE 17

A patient is diagnosed as requiring treatment for glutamate regulation. The patient may then be administered an effective amount of the compounds of the present invention, such as set forth in example 1–3. It would be expected that the patient's prognosis would improve, the patient would be protected from injury associated with glutamate regulation or the patient would recover from the disease requiring the treatment.

EXAMPLE 18

A patient is suffering from or has suffered a nervous insult, such as that arising from a neurodegenerative disease or neurodegenerative process. The patient may then be administered an effective amount of the compounds of the present invention, such as set forth, in example 1–3. It would be expected that the patient would be protected from further injury or would recover from the nervous insult.

EXAMPLE 19

A patient is suffering from Parkinson's disease. The patient may then be administered an effective amount of the compounds of the present invention, such as set forth in example 1–3. It would be expected that the patient would be protected from further neurodegeneration or would recover from the disease.

EXAMPLE 20

A patient is suffering from amyotrophic lateral sclerosis. The patient may then be administered an effective amount of the compounds of the present invention, such as set forth in example 1–3. It would be expected that the patient would be protected from further neurodegeneration or would recover from the disease.

EXAMPLE 21

A patient is suffering from epilepsy. The patient may then be administered an effective amount of the compounds of the present invention, such as set forth in example 1–3. It would be expected that the patient would be protected from further neurodegeneration or would recover from the disease.

EXAMPLE 22

A patient is suffering from abnormalities in myelination/demyelination processes. The patient may then be administered an effective amount of the compounds of the present invention, such as set forth in example 1–3. It would be expected that the patient would be protected from further neurodegeneration or would recover from the disease.

EXAMPLE 23

A patient is diagnosed as suffering from a cerebrovascular accident, such as stroke. The patient may then be administered an effective amount of the compounds of the present invention, such as set forth in examples 1–3. It would be expected that after the treatment the patient would be significantly protected from or would recover from injury due to the cerebrovascular accident.

EXAMPLE 24

A patient is diagnosed as suffering from a head trauma. The patient may then be administered an effective amount of the compounds of the present invention, such as set forth in examples 1–3. It would be expected that after the treatment the patient would be significantly protected from or would recover from injury due to an ischemic brain, spinal, or peripheral injury resulting from the head trauma.

EXAMPLE 25

A patient is diagnosed as suffering from a spinal trauma. The patient may then be administered an effective amount of the compounds of the present invention, such as set forth in examples 1–3. It would be expected that after the treatment the patient would be significantly protected from or would recover from ischemic injury resulting from the spinal trauma.

EXAMPLE 26

A patient is going to undergo surgery. The patient may then be administered an effective amount of the compounds of the present invention, such as set forth in examples 1–3. It would be expected that after the treatment the patient would not develop an ischemic brain, spinal, or peripheral injury resulting from or associated with the surgery.

EXAMPLE 27

A patient is diagnosed as suffering from focal ischemia, such as that associated with thromboembolytic occlusion of a cerebral vessel,, traumatic head injury, edema or brain tumors. The patient may then be administered an effective amount of the compounds of the present invention, such as set forth in examples 1–3. It would be expected that after the treatment the patient would be significantly protected from or would recover from brain, spinal, or peripheral injury resulting from focal ischemia.

EXAMPLE 28

A patient is diagnosed as suffering from global ischemia. The patient may then be administered an effective amount of the compounds of the present invention, such as set forth in examples 1–3. It would be expected that after the treatment the patient would be significantly protected from or would recover from a brain, spinal, or peripheral injury resulting from global ischemia.

EXAMPLE 29

A patient is diagnosed as suffering from a cardiac arrest. The patient may then be administered the compounds of the present invention, such as set forth in examples 1–3. It would be expected that after the treatment the patient would be significantly protected from or would recover from an ischemic brain, spinal, or peripheral injury associated with cardiac arrest.

EXAMPLE 30

A patient is diagnosed as suffering from hypoxia, asphyxia or perinatal asphyxia. The patient may then be administered the compounds of the present invention, such as set forth in examples 1–3. It would be expected that after the treatment the patient would be significantly protected from or would recover from an ischemic brain, spinal, or peripheral injury associated with the hypoxia, asphyxia or perinatal asphyxia.

EXAMPLE 31

A patient is diagnosed as suffering from a cerebro-cortical injury. The patient may then be administered the compounds of the present invention, such as set forth in examples 1–3. It would be expected that after the treatment the patient would be significantly protected from or would recover from an ischemic brain injury resulting from the cerebro-cortical injury.

EXAMPLE 32

The patient is diagnosed as suffering from an injury to the caudate nucleus. The patient may then be administered the compounds of the present invention, such as set forth in examples 1–3. It would be expected that after the treatment the patient would be significantly protected from or would recover from an ischemic brain injury resulting from the injury to the caudate nucleus.

EXAMPLE 33

A patient is diagnosed with a condition as shown in examples 13–32. The compounds of the present invention may then be administered to the patient intravenously, intramuscularly, intraventricularly to the brain, rectally, subcutaneously, intranasally, through a catheter with or without a pump, placed adjacent or near tissue damaged by an ischemic event, orally, through a transdermal patch and/or topically, or through a polymer implant located adjacent to or near tissue damaged by an ischemic event. The patient's condition would be expected to improve.

EXAMPLE 34

A patient is diagnosed with a condition as shown in examples 13–32. The compounds of the present invention may then be administered to the patient through a 100 mg/kg bolus. This may be followed by a 20 mg/kg intravenous infusion per hour over a two-hour period. The patient's condition would be expected to improve.

EXAMPLE 35

A patient is diagnosed with an cortical injury due to a condition such as set forth in Examples 13–32. The patient may then be administered the compounds of the present invention, such as set forth in examples 1–3. It would be expected that the patient would be significantly protected from further injury, or would exhibit at least 65% to at least 80% recovery from the injury after treatment.

The invention being thus described, it will be obvious that the same may be varied in many ways. Such variations are not to be regarded as a departure from the spirit and scope of the invention and all such modifications are intended to be included with the scope of the present invention.

What is claimed is:

1. A method for treating glutamate abnormalities which comprises administering an effective amount of a NAALADase inhibitor to an animal, wherein the NAALADase inhibitor is a compound having the formula:

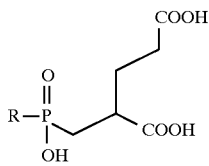

where

R is hydroxy, $C_1$–$C_9$ straight or branched chain alkyl or alkenyl group, $C_3$–$C_8$ cycloalkyl, $C_5$–$C_7$ cycloalkenyl, or $Ar_1$, wherein said alkyl, alkenyl, cycloalkyl, cycloalkenyl or $Ar_1$ group is optionally substituted with $C_3$–$C_8$ cycloalkyl, $C_5$–$C_7$ cycloalkenyl, $C_1$–$C_4$ alkyl, $C_1$–$C_4$ alkenyl, hydroxy, halo, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or $Ar_1$, and where $Ar_1$ is selected from the group consisting of naphthyl, or phenyl, having one to three substituents which are independently selected from the group consisting of hydrogen, halo, hydroxy, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;

or a pharmaceutically acceptable salt, hydrate, or a mixture thereof.

2. A method for treating glutamate abnormalities which comprises administering an effective amount of a NAALADase inhibitor to an animal, wherein the NAALADase inhibitor is selected from the group consisting of:

2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid;
2-[[butylhydroxyphosphinyl]methyl]pentanedioic acid;
2-[[cyclohexylhydroxyphosphinyl]methyl]pentanedioic acid;
2-[[phenylhydroxyphosphinyl]methyl]pentanedioic acid;
2-[[2-(tetrahydrofuranyl)hydroxyphosphinyl]methyl] pentanedioic acid;
2-[[(2-tetrahydropyranyl)hydroxyphosphinyl]methyl] pentanedioic acid;
2-[[((4-pyridyl)methyl)hydroxyphosphinyl]methyl] pentanedioicacid;
2-[[((2-pyridyl)methyl)hydroxyphosphinyl]methyl] pentanedioicacid;
2-[[(phenylmethyl)hydroxyphosphinyl]methyl]pentanedioic acid;
2-[[((2-phenylethyl)methyl)hydroxyphosphinyl]methyl] pentanedioic acid;

2-[[((3-phenylpropyl)methyl)hydroxyphosphinyl]methyl] pentanedioic acid;
2-[[((3-phenylbutyl)methyl)hydroxyphosphinyl]methyl] pentanedioic acid;
2-[[((2-phenylbutyl)methyl)hydroxyphosphinyl]methyl] pentanedioic acid;
2-[[(4-phenylbutyl)hydroxyphosphinyl]methyl] pentanedioic acid; and
2-[[(aminomethyl)hydroxyphosphinyl]methyl]pentanedioic acid.

3. A method for treating glutamate abnormalities which comprises administering an effective amount of a NAALADase inhibitor to an animal, wherein the NAALADase inhibitor is selected from the group consisting of:
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid; and
2-[[phenylhydroxyphosphinyl]methyl]pentanedioic acid.

4. A method for treating glutamate abnormalities which comprises administering an effective amount of a NAALADase inhibitor to an animal, wherein the NAALADase inhibitor is selected from the group consisting of:
2-(phosphonomethyl)pentanedioic acid;
2-(phosphonomethyl)succinic acid; and,
2-[[(2-carboxyethyl)hydroxyphosphinyl]methyl] pentanedioic acid.

5. A method for treating glutamate abnormalities which comprises administering an effective amount of a NAALADase inhibitor to an animal, wherein the NAALADase inhibitor is 2-(phosphonomethyl)pentanedioic acid.

6. The method of claim 1, wherein the effective amount of a NAALADase inhibitor is administered in combination with an additional therapeutic agent.

7. A method for treating ischemia which comprises: administering an effective amount of a NAALADase inhibitor to an animal suffering from ischemia, wherein the NAALADase inhibitor is a compound having the formula:

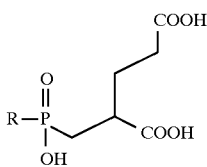

where
R is hydroxy, $C_1$–$C_9$ straight or branched chain alkyl or alkenyl group, $C_3$–$C_8$ cycloalkyl, $C_5$–$C_7$ cycloalkenyl, or $Ar_1$,
wherein said alkyl, alkenyl cycloalkyl, cycloalkenyl or $Ar_1$ group is optionally substituted with $C_3$–$C_8$ cycloalkyl, $C_5$–$C_7$ cycloalkenyl, $C_1$–$C_4$ alkyl, $C_1$–$C_4$ alkenyl, hydroxy, halo, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or $Ar_1$, and where $Ar_1$ is selected from the group consisting of napthyl, indolyl, furyl, thienyl, pyridyl, or phenyl, having one to three substituents which are independently selected from the group consisting of hydrogen, halo, hydroxy, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;
or a pharmaceutically acceptable salt, hydrate, or a mixture thereof.

8. A method for treating ischemia which comprises: administering an effective amount of a NAALADase inhibitor to an animal suffering from ischemia, wherein the NAALADase inhibitor is selected from the group consisting of:
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid;
2-[[butylhydroxyphosphinyl]methyl]pentanedioic acid;
2-[[cyclohexylhydroxyphosphinyl]methyl]pentanedioic acid;
2-[[phenylhydroxyphosphinyl]methyl]pentanedioic acid;
2-[[2-(tetrahydrofuranyl)hydroxyphosphinyl]methyl] pentanedioic acid;
2-[[(2-tetrahydropyranyl)hydroxyphosphinyl]methyl] pentanedioic acid;
2-[[((4-pyridyl)methyl)hydroxyphosphinyl]methyl] pentanedioicacid;
2-[[((2-pyridyl)methyl)hydroxyphosphinyl]methyl] pentanedioicacid;
2-[[(phenylmethyl)hydroxyphosphinyl]methyl]pentanedioic acid;
2-[[((2-phenylethyl)methyl)hydroxyphosphinyl]methyl] pentanedioic acid;
2-[[((3-phenylpropyl)methyl)hydroxyphosphinyl]methyl] pentanedioic acid;
2-[[((3-phenylbutyl)methyl)hydroxyphosphinyl]methyl] pentanedioic acid;
2-[[((2-phenylbutyl)methyl)hydroxyphosphinyl]methyl] pentanedioic acid;
2-[[(4-phenylbutyl)hydroxyphosphinyl]methyl] pentanedioic acid; and
2-[[(aminomethyl)hydroxyphosphinyl]methyl]pentanedioic acid.

9. A method for treating ischemia which comprises: administering an effective amount of a NAALADase inhibitor to an animal suffering from ischemia, wherein the NAALADase inhibitor is selected from the group consisting of:
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid; and
2-[[phenylhydroxyphosphinyl]methyl]pentanedioic acid.

10. A method for treating ischemia which comprises: administering an effective amount of a NAALADase inhibitor to an animal suffering from ischemia, wherein the NAALADase inhibitor is selected from the group consisting of:
2-(phosphonomethyl)pentanedioic acid;
2-(phosphonomethyl)succinic acid; and,
2-[[(2-carboxyethyl)hydroxyphosphinyl]methyl] pentanedioic acid.

11. A method for treating ischemia which comprises: administering an effective amount of a NAALADase inhibitor to an animal suffering from ischemia, wherein the NAALADase inhibitor is 2-(phosphonomethyl)pentanedioic acid.

12. The method of claim 7, wherein the effective amount of a NAALADase inhibitor is administered in combination with an additional therapeutic agent.

* * * * *

UNITED STATES PATENT AND TRADEMARK OFFICE
CERTIFICATE OF CORRECTION

PATENT NO. : 5,824,662
DATED : October 20, 1998
INVENTOR(S) : Barbara S. Slusher and Paul F. Jackson It is certified that error appears in the above-identified patent and that said Letters Patent is hereby corrected as shown below:

Column 30, claim 1,
Please replace lines 15-44 with Claim 1 as follows:
-- 1. A method for treating glutamate abnormalities which comprises administering an effective amount of a NAALADase inhibitor to an animal, wherein the NAALADase inhibitor is a compound having the formula:

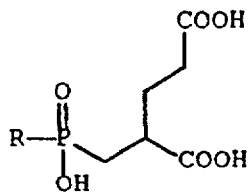

where
R is hydroxy, $C_1$-$C_9$ straight or branched chain alkyl, $C_2$-$C_9$ straight or branched chain alkenyl group, $C_3$-$C_8$ cycloalkyl, $C_5$-$C_7$ cycloalkenyl, phenyl, naphthyl, or phenyl ($C_1$-$C_4$ alkyl), wherein said alkyl, alkenyl, cycloalkyl, cycloalkenyl, phenyl, naphthyl, or phenyl ($C_1$-$C_4$ alkyl) group is optionally substituted with $C_3$-$C_8$ cycloalkyl, $C_5$-$C_7$ cycloalkenyl, hydroxy, halo, nitro, trifluoromethyl, $C_1$-$C_6$ straight or branched chain alkyl, $C_2$-$C_6$ straight or branched chain alkenyl, $C_1$-$C_4$ alkoxy, $C_1$-$C_4$ alkenyloxy, phenoxy, benzyloxy, amino, or $Ar_1$, and where $Ar_1$ is selected from the group consisting of naphthyl and phenyl, having one to three substituents which are independently selected from the group consisting of hydrogen, halo, hydroxy, nitro, trifluoromethyl, $C_1$-$C_6$ straight or branched alkyl, $C_2$-$C_6$ straight or branched chain alkenyl, $C_1$-$C_4$ alkoxy or $C_2$-$C_4$ alkenyloxy, phenoxy, benzyloxy, and amino;
or a pharmaceutically acceptable salt, hydrate, or a mixture thereof.--

UNITED STATES PATENT AND TRADEMARK OFFICE
CERTIFICATE OF CORRECTION

PATENT NO.    : 5,824,662
DATED         : October 20, 1998
INVENTOR(S)   : Barbara S. Slusher and Paul F. Jackson It is certified that error appears in the above-identified patent and that said Letters Patent is hereby corrected as shown below:

Please replace Claim 2, column 30, line 45 to column 31, line 10 with Claim 2 as follows:

-- 2. A method for treating glutamate abnormalities which comprises administering an effective amount of a NAALADase inhibitor to an animal, wherein the NAALADase inhibitor is selected from the group consisting of:
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid;
2-[[butylhydroxyphosphinyl]methyl]pentanedioic acid;
2-[[cyclohexylhydroxyphosphinyl]methyl]pentanedioic acid;
2-[[phenylhydroxyphosphinyl]methyl]pentanedioic acid;
2-[[phenylmethylhydroxyphosphinyl-)methyl]pentanedioic acid-;
2-[[((2-phenylethyl)methyl)hydroxyphosphinyl]methyl]pentanedioic acid;
2-[[((3-phenylpropyl)methyl)hydroxyphosphinyl]methyl]pentanedioic acid;
2-[[((3-phenylbutyl)methyl)hydroxyphosphinyl]methyl]pentanedioic acid;
2-[[((2-phenylbutyl)methyl)hydroxyphosphinyl]methyl]pentanedioic acid;
2-[[((4-phenylbutyl)methyl)hydroxyphosphinyl]methyl]pentanedioic acid; and
2-[[(aminomethyl)hydroxyphosphinyl]methyl]pentanedioic acid. --

UNITED STATES PATENT AND TRADEMARK OFFICE
CERTIFICATE OF CORRECTION

PATENT NO. : 5,824,662
DATED : October 20, 1998
INVENTOR(S) : Barbara S. Slusher and Paul F. Jackson It is certified that error appears in the above-identified patent and that said Letters Patent is hereby corrected as shown below:

Please replace Claim 7, column 31, lines 33-63 with Claim 7 as follows:
-- 7. A method for treating ischemia which comprises: administering an effective amount of a NAALADase inhibitor to an animal suffering from ischemia, wherein the NAALADase inhibitor is a compound having the formula:

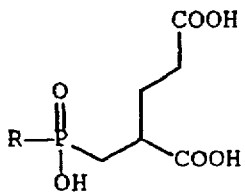

where
R is hydroxy, $C_1$-$C_9$ straight or branched chain alkyl, $C_2$-$C_9$ straight or branched chain alkenyl group, $C_3$-$C_8$ cycloalkyl, $C_5$-$C_7$, cycloalkenyl, phenyl, naphthyl, or phenyl ($C_1$-$C_4$ alkyl), wherein said alkyl, alkenyl, cycloalkyl, cycloalkenyl, phenyl, naphthyl, or phenyl ($C_1$-$C_4$ alkyl) group is optionally substituted with $C_3$-$C_8$ cycloalkyl, $C_5$-$C_7$, cycloalkenyl, hydroxy, halo, nitro, trifluoromethyl, $C_1$-$C_6$ straight or branched chain alkyl, $C_2$-$C_6$ straight or branched chain alkenyl, $C_1$-$C_4$ alkoxy, $C_2$-$C_4$ alkenyloxy, phenoxy, benzyloxy, amino, or $Ar_1$, and where $Ar_1$ is selected from the group consisting of naphthyl and phenyl, having one to three substituents which are independently selected from the group consisting of hydrogen, halo, hydroxy, nitro, trifluoromethyl, $C_1$-$C_6$ straight or branched alkyl, $C_2$-$C_6$ straight or branched chain alkenyl, $C_1$-$C_4$ alkoxy, $C_2$-$C_4$ alkenyloxy, phenoxy, benzyloxy, and amino;
or a pharmaceutically acceptable salt, hydrate, or a mixture thereof. --

UNITED STATES PATENT AND TRADEMARK OFFICE
CERTIFICATE OF CORRECTION

PATENT NO. : 5,824,662
DATED : October 20, 1998
INVENTOR(S) : Barbara S. Slusher and Paul F. Jackson It is certified that error appears in the above-identified patent and that said Letters Patent is hereby corrected as shown below:

Please replace Claim 8, column 32, lines 1-34 with Claim 8 as follows:

-- 8. A method for treating ischemia which comprises: administering an effective amount of a NAALADase inhibitor to an animal suffering from ischemia, wherein the NAALADase inhibitor is selected from the group consisting of:
2-[[methylhydroxyphosphinyl]methyl]pentanedioic acid;
2-[[ethylhydroxyphosphinyl)methyl]pentanedioic acid;
2-[[propylhydroxyphosphinyl]methyl]pentanedioic acid;
2-[[butylhydroxyphosphinyl]methyl]pentanedioic acid;
2-[[cyclohexylhydroxyphosphinyl]methyl]pentanedioic acid;
2-[[phenylhydroxyphosphinyl]methyl]pentanedioic acid;
2-[[phenylmethylhydroxyphosphinyl]methyl]pentanedioic acid;
2-[[((2-phenylethyl)methyl),hydroxyphosphinyl]methyl] pentanedioic acid;
2-[[((3-phenylpropyl)methyl)hydroxyphosphinyl]methyl] pentanedioic acid;
2-[[((3-phenylbutyl)methyl)hydroxyphosphinyl]methyl] pentanedioic acid;
2-[[((2-phenylbutyl)methyl)hydroxyphosphinyl]methyl] pentanedioic acid;
2-[[((4-phenylbutyl)methyl)hydroxyphosphinyl]methyl] pentanedioic acid; and
2-[[(aminomethyl)hydroxyphosphinyl]methyl]pentanedioic acid. --

Signed and Sealed this

Eighteenth Day of December, 2001

Attest:

*Attesting Officer*

JAMES E. ROGAN
*Director of the United States Patent and Trademark Office*